United States Patent [19]

Takeshita et al.

[11] 4,022,891
[45] May 10, 1977

[54] NOVEL 1α,24-DIHYDROXYCHOLECALCIFEROL COMPOSITIONS, NOVEL PRECURSORS THEREOF, AND PROCESSES FOR PREPARING THEM

[75] Inventors: Toru Takeshita, Hino; Yoshinobu Hashimoto, Fujisawa; Hiroyuki Kawashima, Hino; Sachio Ishimoto, Tokyo; Nobuo Ikekawa, Tokyo; Masuo Morisaki, Tokyo, all of Japan

[73] Assignee: Teijin Limited, Osaka, Japan

[22] Filed: June 2, 1975

[21] Appl. No.: 583,115

[30] Foreign Application Priority Data

| June 18, 1974 | Japan | 49-68664 |
| Dec. 9, 1974 | Japan | 49-141329 |
| Dec. 9, 1974 | Japan | 49-141330 |
| Dec. 9, 1974 | Japan | 49-141331 |
| Dec. 9, 1974 | Japan | 49-141332 |
| Dec. 27, 1974 | Japan | 49-149017 |
| Dec. 27, 1974 | Japan | 49-149018 |
| Dec. 27, 1974 | Japan | 49-149020 |
| Dec. 27, 1974 | Japan | 49-149021 |
| Dec. 27, 1974 | Japan | 49-149022 |

[52] U.S. Cl. .................... 424/236; 260/397.2; 260/239.55 R
[51] Int. Cl.² ........................ A61K 31/59
[58] Field of Search ........ 260/239.55, 397.2, 397.1

[56] References Cited

UNITED STATES PATENTS

| 3,901,928 | 8/1975 | Hesse et al. | 260/397.2 |
| 3,928,397 | 12/1975 | Ikekawa et al. | 260/397.2 |

*Primary Examiner*—Elbert L. Roberts
*Attorney, Agent, or Firm*—Sherman & Shalloway

[57] ABSTRACT

Novel 1α, 24-dihydroxycholecalciferol and derivatives thereof which are useful with reduced side-effects for the treatment of abnormal metabolism of calcium and phosphorus caused by liver failure, renal failure, gastrointestinal tract failure and parathyroid failure, and related bone diseases. Preparation of the novel 1α, 24-dihydroxycholecalciferol and their derivatives starts from 1α, 24-dihydroxycholesterol prepared by reacting 1α, 2α-epoxy-24-keto-cholesta-4,6-dien-3-one with an alkali metal and a proton donor in the presence of liquid ammonia or a liquid amine. Reaction of the 1α, 24-dihydroxycholesterol with an allylic brominating agent, followed by contacting with a dehydrobrominating agent, affords 1α,3β, 24-trihydroxycholesta-5,7-diene derivative, which can then be converted to 1α, 24-dihydroxycholocalciferol by ultraviolet irradiation in an organic solvent, followed by isomerization. Processes are also provided for separating 1α, 24-dihydroxycholesterol into an (S)-epimer and an (R)-epimer, and also for separating at least one of 1α, 3β, 24(S)-and 1α, 3β, 24(R)-trihydroxycholesta-5,7-dienes from trihydroxycholesta-4,6-diene.

36 Claims, 7 Drawing Figures

MASS SPECTRUM OF 1α, 24-DIHYDROXYCHOLESTEROL

Figure 1:
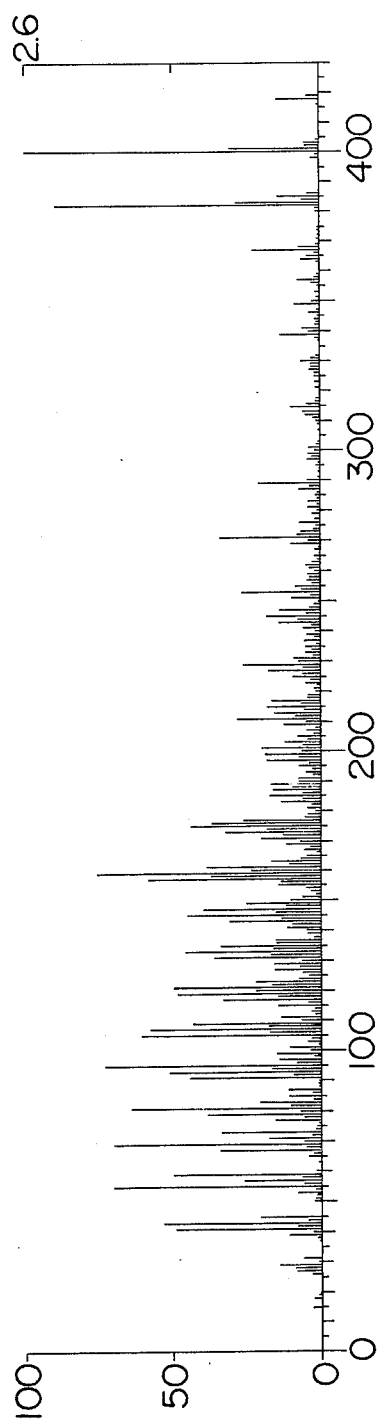

Fig. 1  MASS SPECTRUM OF 1α, 24-DIHYDROXYCHOLESTEROL

Figure 3:
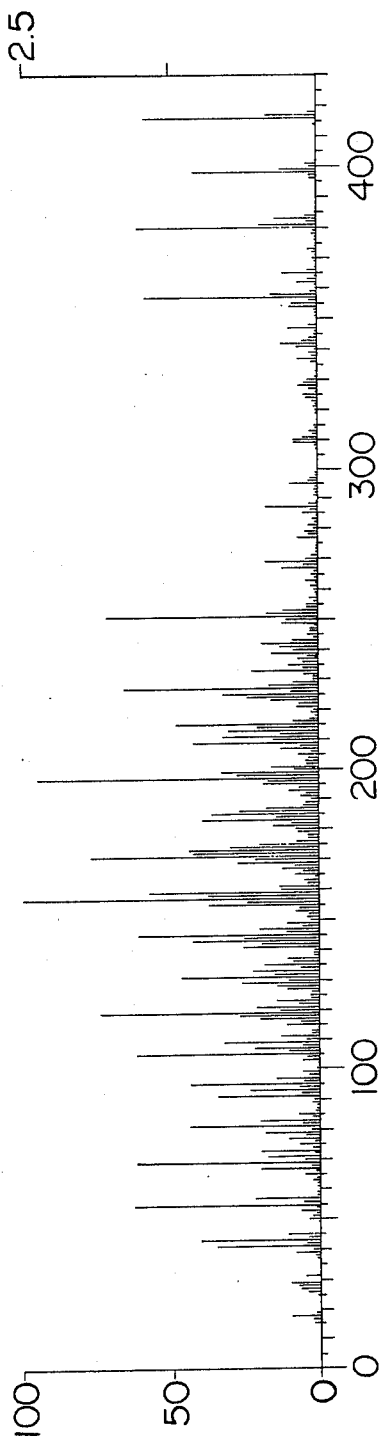

Fig. 3 MASS SPECTRUM OF 1α, 3β, 24-TRIHYDROXYCHOLESTA-5, 7-DIENE

Figure 4:
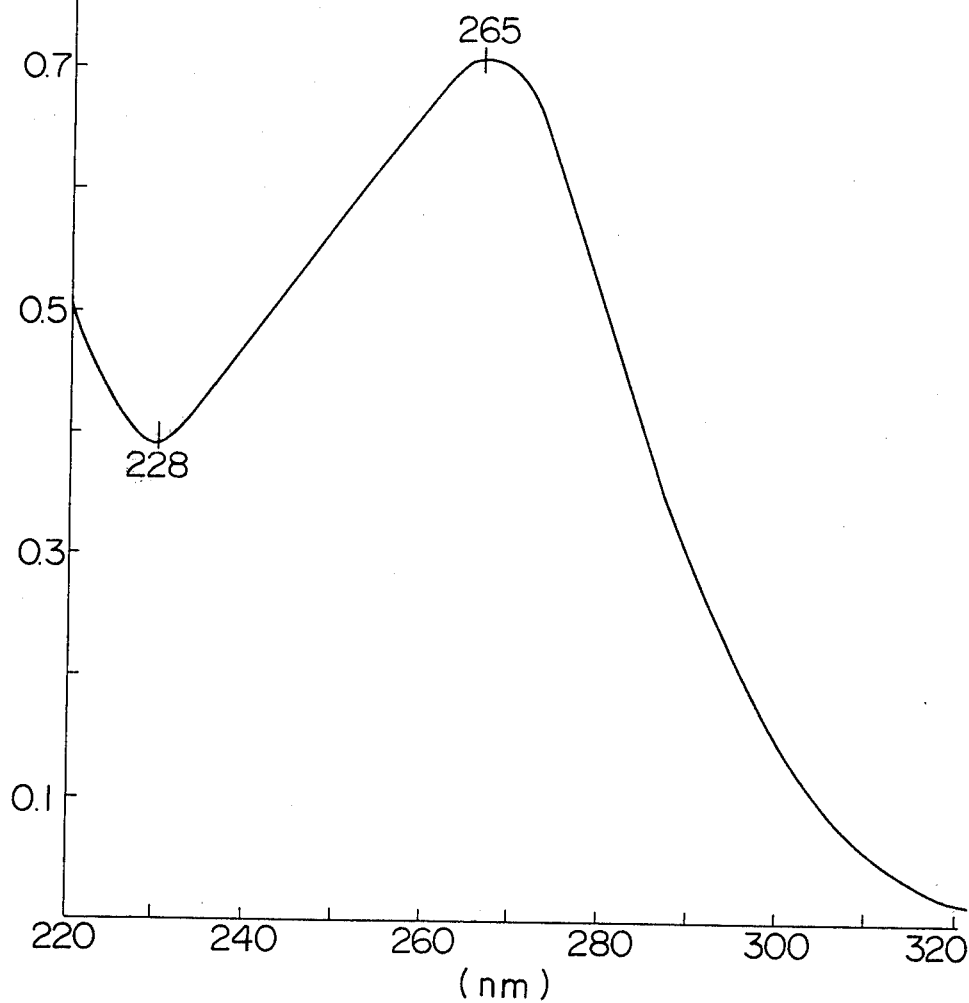

Fig. 4 UV SPECTRUM OF 1α,24-DIHYDROXYCHOLECALCIFEROL

MASS SPECTRUM OF 1α,24-DIHYDROXYCHOLECALCIFEROL

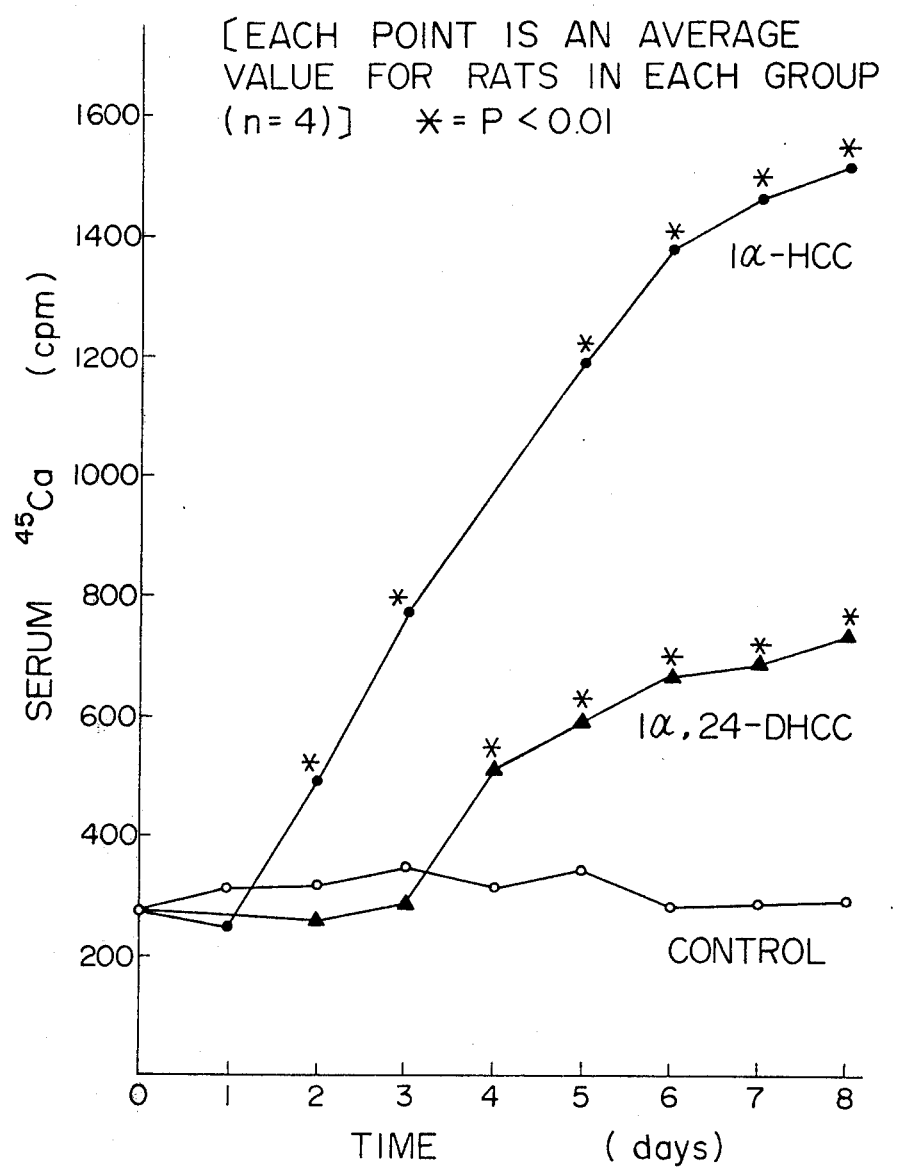

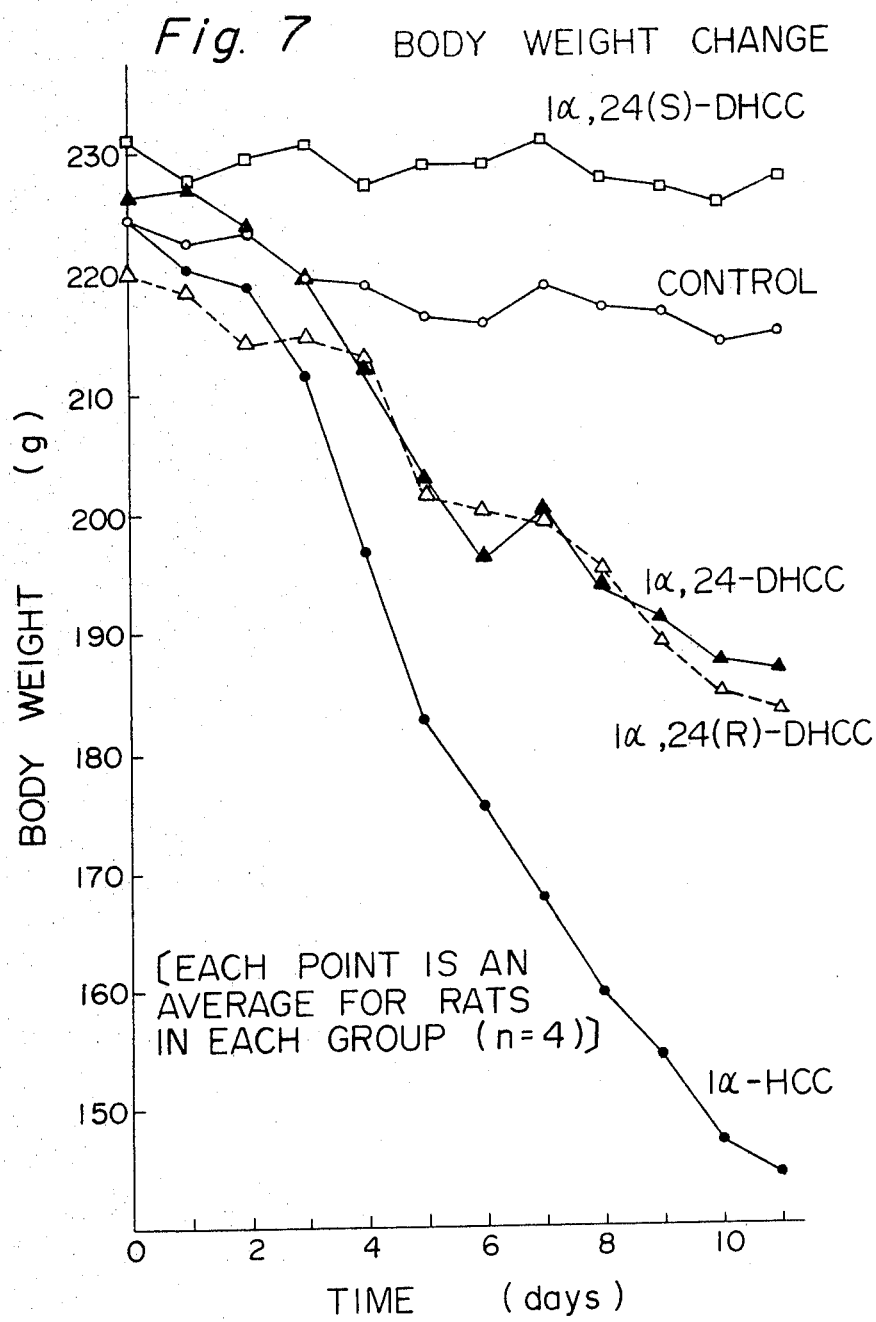

NOVEL 1α,24-DIHYDROXYCHOLECALCIFEROL COMPOSITIONS, NOVEL PRECURSORS THEREOF, AND PROCESSES FOR PREPARING THEM

This invention relates to novel 1α, 24-dihydroxycholecalciferols, derivatives thereof, novel precursors thereof, and processes for preparing them.

The invention also relates to a pharmaceutical composition for warm-blooded animals which comprises a pharmaceutically effective amount of the novel 1α,24-dihydroxycholecalciferols, and a method for controlling the calcium metabolism of warm-blooded animals which comprises administering a pharmaceutically effective amount of the 1α,24-dihydroxycholecalciferol.

The novel 1α,24-dihydroxycholecalciferols and derivatives thereof are expressed by the following formula

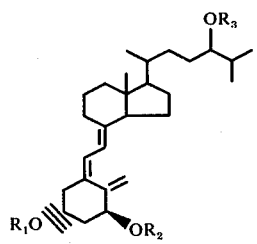

(5)

wherein $R_1$, $R_2$ and $R_3$ are identical or different, and represent a hydrogen atom or a protective group convertible to hydrogen.

The formula (5) generically represents 1α,24(S)-dihydroxycholecalciferol and its derivative (to be referred to as 1α,24(S)-DHCC and its derivatives) of the following formula

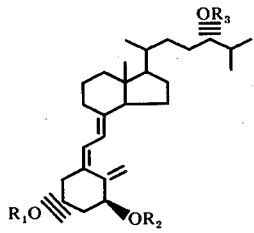

(5-1)

wherein $R_1$, $R_2$ and $R_3$ are the same as defined above, 1α,24(R)-dihydroxycholecalciferol and its derivatives (to be referred to as 1α,24(R)-DHCC and its derivatives) of the following formula,

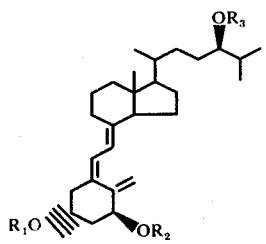

(5-2)

wherein $R_1$, $R_2$ and $R_3$ are the same as defined above, and a mixture of a 1α,24(S)-epimer of formula (5-1) and a 1α,24(R)-epimer of the formula (5-2).

In the present specification, the above mixture of a 1α,24(S)-epimer of formula (5-1) and a 1α,24(R)- epimer of formula (5-2) in optional ratio is expressed by the following formula

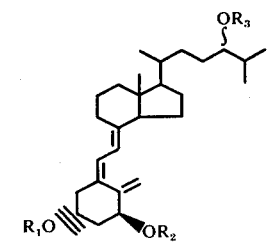

(5-3)

In other words, -OR$_3$ at the 24-position is expressed by

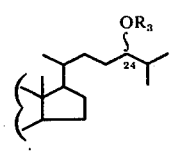

The same representation as in the above formulae (5), (5-1) and (5-2) is used to express precursors of these compounds.

Of the 1α,24-dihydroxycholecalciferols and its derivatives of formula (5), 1α,24-dihydroxycholecalciferols of the formula

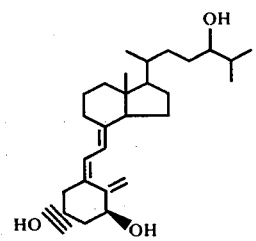

(5-a)

have most useful pharmacological effects, as has been ascertained by the work of the inventors of the present application.

The 1α,24-dihydroxycholecalciferols of formula (5-a) also represent (i) 1α,24(S)-dihydroxycholecalciferol[1α,24(S)-DHCC], (ii) 1α,24(R)-dihydroxycholecalciferol [1α,24(R)-DHCC], and (iii) a mixture of 1α,24(S)-DHCC and 1α,24(R)-DHCC [1α,24-DHCC epimeric mixture].

As will be shown hereinbelow by detailed animal tests, the 1α,24(S)-DHCC alone, the 1α,24(R)-DHCC alone, and a mixture of these all show a very useful pharmacological activity as a controlling agent for the calcium metabolism of warm-blooded animals, and have a far lower toxicity (LD$_{50}$) than 1α-hydroxycholecalciferol (1α-HCC) which is a known analog of active forms of vitamin D$_3$.

The 1α-hydroxycholecalcifrol (1α-HCC) is expressed by the following formula

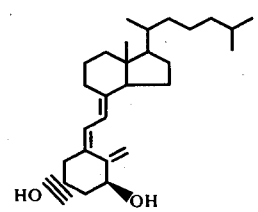

(B-1)

To the best of our knowledge, there has been no report on the above 1α,24-dihydroxycholecalciferols, and the only exception is the report of the present inventors in The Journal of Steroid Biochemistry, Vol. 5, No. 4, June 1974 - Fourth International Congress on Hormonal Steroids - Mexico City, Sept. 2-7, 1974, Abstracts of Papers Presented (actually published on Aug. 16, 1974). The report states that 24-hydroxycholesterol (24-HC) of the following formula

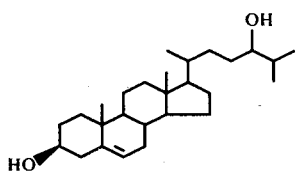

(B-2)

24,25-dihydroxycholesterol (24,25-DHC) of the following formula

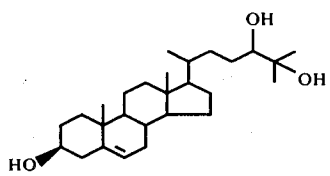

(B-3)

and their 1α-hydroxy derivatives can be converted to vitamin D derivatives by conventional established procedures. However, it was only the compounds of formula (B-2) and (B-3) which the inventors could then convert to vitamin D derivatives. Accordingly, in the above-cited Congress in Mexico City, they only stated that the conversion of the 1α-hydroxy derivatives of (B-2) to vitamin D derivatives were still under investigation, and did not give any report on the conversion of the 1α-hydroxy derivatives of (B-3) to vitamin D derivatives. According to the works of the inventors made then and their subsequent investigations, the procedures known prior to the filing of the present invention could not afford vitamin D derivatives cholecalciferol-type from these 1α-hydroxy derivatives, as will be mentioned below. Now, however, the inventors succeeded in synthesizing a group of novel 1α-24-dihydroxycholecalciferol and its derivatives of formula (5), preferably, formula (5-a) by the process of this invention to be described hereinbelow.

The process of this invention will be described below in detail.

1. First Reaction Step

According to this invention, 1α-24-dihydroxycholesterol (to be referred to as 1α-24-DHC) of the following formula (2-a)

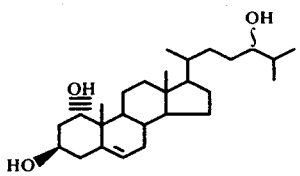

(2-a)

is prepared by reacting 1α-2α-epoxy-24-ketocholesta-4,6-dien-3-one (to be referred to as 1α-2α-epoxy) of the following formula

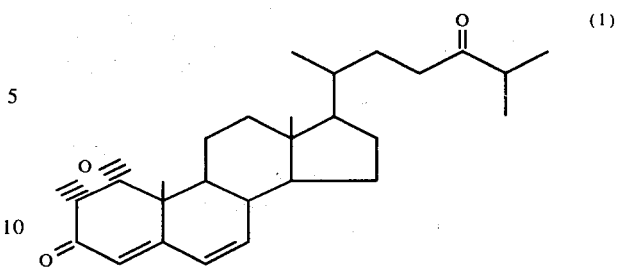

(1)

with an alkali metal and a proton donor in the presence of liquid ammonia or a liquid amine.

1α,24-DHC expressed by formula (2-a) means a mixture of 1α,24(S)-dihydroxycholesterol [1α,24(S)-DHC] and 1α,24(R)-dihydroxycholesterol [1α,24(R)-DHC] in optional ratios, and according to the method of the above first step, 1α,24-DHC is obtained as a mixture of (S)-epimer and (R)-epimer.

To the best of our knowledge, the 1α,24-epoxy of formula (1) and 1α,24-DHC of formula (2-a) are both novel compounds not described in the prior literature, but synthesized for the first time by the inventors of the present application.

The above 1α,24-DHC can be converted to a group of 1α,24-DHCC and its derivatives of formula (5), especially formula (5-a), by the process of this invention to be described. In addition, these compounds are useful intermediates for other steroids having physiological activatives, for example, intermediates for the synthesis of 1α,24,25-trihydroxycholecalciferol which is an active form of vitamin $D_3$.

Examples of the liquid amines used in the first step are primary, secondary or tertiary alkylamines such as methylamine, ethylamine, diethylamine, or triethylamine. The use of liquid ammonia is preferred, however. Although there is no particular restriction on the liquid ammonia, it is preferably treated, for example, by distillation, to remove water from it as much as possible. The suitable amount of the liquid ammonia or the liquid amine is 5 to 500 times, especially 10 to 200 times, the weight of the 1α,2α-epoxy-24-ketocholesta-4,6-dien-3-one.

Examples of preferred alkali metals are lithium, sodium, and potassium. Lithium is especially suitable. The amount of the alkali metal is excessive with regard to the 1α,2α-epoxy of formula (1), for example, 5 to 250 times (atomic equivalent), especially 10 to 200 times, the amount of the 1α,2α-epoxy of formula (1).

Preferably, an inert organic solvent for the 1α,2α-epoxy of formula (1) is used in order to have the reaction proceed smoothly. Examples of preferred solvents are ethers such as ethyl ether, tetrahydrofuran, dioxane or 1,2-dimethoxyethane, aliphatic hydrocarbons such as ligroine, pentane, hexane, cyclohexane or methyl cyclohexane, and mixtures of two or more of these.

The amount of the organic solvent is at least equal to the volume of the liquid ammonia used, preferably 1 to 2 times the volume of the liquid ammonia.

Suitable proton donors are ammonium salts such as ammonium salts of organic acids and ammonium salts of of inorganic acids. Specific examples of the ammonium salts are ammonium chloride, ammonium bromide, ammonium carbonate, ammonium sulfate, ammonium phosphate, ammonium hydrogenphosphate, ammonium acetate, ammonium formate, ammonium benzoate, ammonium benzenesulfonate, and ammonium p-toluenesulfonate. Of these, the ammonium salts of inorganic acids, such as ammonium chloride, are especially preferred. The amount of the ammonium salt is at least equimolar to the alkali metal used, preferably up to 10 molar times the latter.

Lower alcohols such as methanol, ethanol or tert-butyl alcohol can also be used as the proton donor.

The method of adding the reaction reagents is very important in performing the first step of the process of this invention, and advantageously, any one of the following three adding methods is chosen.

A. the 1α,2α-epoxy is added to a mixture containing liquid ammonia and the alkali metal, and then the ammonium salt is added. At this time, it is more preferred to add the ammonium salt successively in two or more small portions.

B. A minor proportion (desirably less than 0.7 molar time the amount of the alkali metal used) of the ammonium salt is previously added to a mixture containing the liquid ammonia and the alkali metal. The 1α,2α-epoxy is added to this system, and then the remainder of the ammonium salt is added.

C. The 1α,2α-epoxy and the ammonium salt are added simultaneously in small portions to a mixture containing the liquid ammonia and the alkali metal.

Of the above methods, the method (A) is especially preferred.

The reaction temperature is usually from −70° to the refluxing temperature of liquid ammonia in the reaction system.

It is advantageous that after adding all of the proton donor, the reaction is carried out until the alkali metal used in excess is completely decomposed under reflux of the liquid ammonia. This can afford the final 1α,24-DHC in a higher yield.

A process has previously been known which comprises reacting 1α,2α-epoxy-cholesta-4,6-dien-3-one of the formula

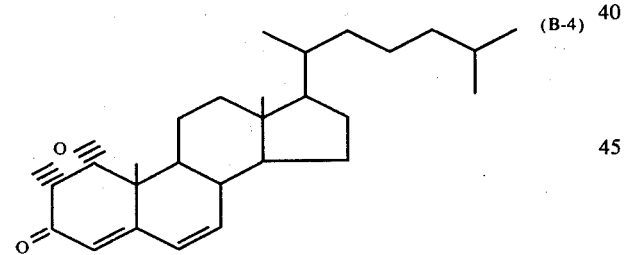

(B-4)

with metallic lithium and ammonium chloride in the presence of liquid ammonia to form 1α-hydroxycholesterol (1α-HC) of the formula

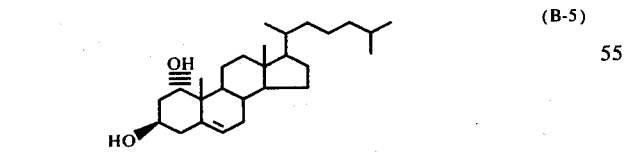

(B-5)

for the purpose of obtaining 1α-hydroxycholecalciferol (b-1) (D. H. R. Barton et al., J. Am. Chem. Soc., 95, 2748, 1973).

It has been found that the 1α,2α-epoxy used in this invention is substituted by an oxo group (=O) at the 24-position, and according to this invention, the four-stage reducing reaction of such a 1α,2α-epoxy, that is, i. the reduction of the carbonyl group at the 24-position, ii. the reduction of the 1α,2α-epoxy group, iii. the reduction of the 4,6-diene to a 5-ene, and iv. the reduction of the carbonyl group at the 3-position, proceeds smoothly in a single step, and that when preferred conditions are employed, 1α,24-dihydroxycholesterol (1α,24-DHC) can be synthesized in a high yield of, say, 60 to 75%. The fact that such a four-stage reducing reaction [stages (i) to (iv)] proceeds smoothly in a single step is neither disclosed in any prior publication, and this is believed to be a novel reaction discovered for the first time by the inventors of the present application.

2. Preparation of the 1α,2α-epoxy

The 1α,2α-epoxy of formula (1) used as a starting material in the first step of the process of this invention can be easily prepared, for example, by the following process using as a starting material fucosterol of the following formula

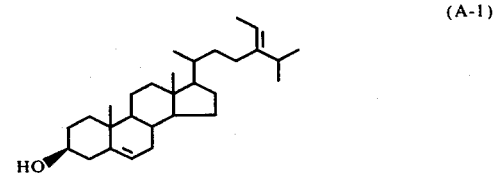

(A-1)

present in great quantities in brown marine algae. One example of this process is as follows:

Fucosterol is oxidized with ozone at low temperatures, and the resulting ozonide is reduced with an acetic acid/zinc system to form 24-ketocholesterol of the following formula

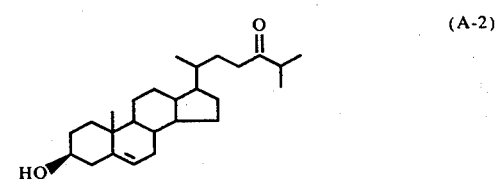

(A-2)

in a yield of about 60 to 75%. The resulting 24-ketocholesterol is oxidized, for example, with 2,3-dichloro-5,6-dicyanobenzoquinone (DDQ) under reflux of, for example, dioxane to form cholesta-1,4,6-triene-3,24-dione of the following formula

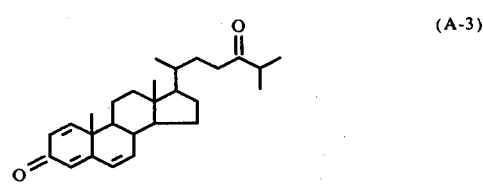

(A-3)

and then this oxidation product is epoxidized at room temperature under alkaline conditions (pH about 7.5–9) using hydrogen peroxide, for example.

This method makes it possible to synthesize the 1α,2α-epoxy of formula (1) in a yield of about 40 to 55% from the 24-ketocholesterol of formula (A-2).

The cholesta-1,4,6-triene-3,24-dione of formula (A-3) is also a novel compound synthesized for the first time by the inventors of the present application.

When a lower alcohol such as methanol is used as a solvent for the above epoxidation reaction, the resulting 1α,2α-epoxy precipitates from the lower alcohol solvent. The precipitated epoxy can be separated from the reaction mixture by filtration, and directly used as a starting material in the first step of the process of this invention.

3. Separation of (S)- and (R)-epimers of 1α,24-DHC

As already stated, the 1α,24-DHC of formula (2) obtained in the first step of the process of this invention is obtained as a mixture of 1α,24(S)-DHC and 1α,24(R)-DHC.

It has been found that according to this invention the (S)-epimer and the (R)-epimer can be separated smoothly by substituted- or unsubstituted-benzoylation of the hydroxyl groups at the 3- and 24-positions of the 1α,24-DHC. In other words, the 1-position may be a hydroxyl group itself or protected by a protective group convertible thereto in order to perform the separation of the (S)- and (R)-epimers.

Substituted- or unsubstituted-benzoylation of the 3- and 24-positions of the 1α,24-DHC can be performed by reacting the 1α,24-DHC with substituted or unsubstituted benzoyl chloride for example in an inert organic solvent in the presence of an organic base as an acid acceptor. This reaction is a conventional reaction known as a Schotten-Baumann reaction. An organic base such as pyridine can be used in the above reaction as the inert organic solvent, and in this case, the use of an acid acceptor is not particularly required.

Substituted- or unsubstituted-benzoylation of the 3- and 24-positions of the 1α,24-DHC can be selectively achieved by reacting it with substituted or unsubstituted benzoyl chloride for example in a pyridine solution at a low temperature (e.g., −5° to 10° C.) for a suitable period of time (e.g., 10 to 24 hours). The hydroxyl group at the 1-position can be acylated by, for example, reacting a sterol whose hydroxyl groups at the 3- and 24-positions are protected, with an acyl chloride in a pyridine solution at 0° to 50° C. The hydroxyl group at the 1-position can be trimethylsilylated, for example, by reacting a sterol whole hydrocyl groups at the 3- and 24-positions are protected, with N-trimethylsilyl imidazole in a pyridine solution at a high temperature (e.g., 50° to 110° C.).

By performing the substituted- or unsubstituted-benzoylation of 1α,24-DHC at higher temperatures, for example, 15° to 100° C., preferably 30° to 80° C., the 1-, 3- and 24-positions of 1α,24-DHC can be benzoylated in one step.

Examples of the substituted or unsubstituted benzoyl groups are benzoyl, p-bromobenzoyl, 2,4-dibromobenzoyl, p-chlorobenzoyl, and p-nitrobenzoyl groups. Of these, benzoyl and p-bromobenzoyl groups are particularly preferred.

The 1-position of 1α,24-DHC may be a hydroxyl group itself. Examples of protective groups for it are the above substituted- or unsubstituted benzoyl groups, acyl groups (organic carboxylic acid residues) or groups capable of forming an ether linkage. Examples of such acyl groups are acetyl, propanoyl, butanoyl, pentanoyl, caproyl, cyclohexanoyl, chloroacetyl, and bromoacetyl groups. Examples of protective groups capable of forming ether linkages with the hydroxyl group at the 1-position are a t.-butyl group, a benzyl group, a triaryl group such as a triphenylmethyl group, a tetrahydropyranyl group, a methoxymethyl group, or an alkyl-substituted silyl group such as a trimethylsilyl group.

The above acyl groups including the substituted or unsubstituted benzoyl groups are preferred as protective groups for the hydroxyl group at the 1-position.

In order to separate the 1α,24-DHC into the (S)-epimer and the (R)-epimer, the 1α,24-DHC of formula (2-a) is first converted to a benzoyl derivative of the 1α,24-DHC expressed by the following formula

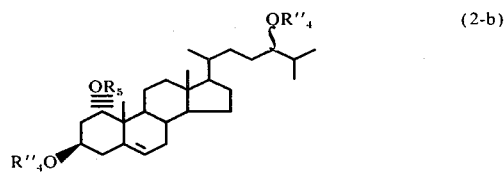

wherein $R''_4$ is a substituted or unsubstituted benzoyl group, and $R_5$ is a hydrogen atom or a protective group convertible to a hydrogen atom.

This benzoyl derivative is then subjected to chromatography using a carrier at least containing silicon dioxide ($SiO_2$) to separate it into a 1α,24(S)-epimer and a 1α,24(R)-epimer.

These epimers are also novel compounds synthesized and separated successfully for the first time by the inventors of the present application.

The carrier containing silicon dioxide may, for example, be silica gel, silicic acid, silica-alumina gel, diatomaceous earth, or kaolin. The silica gel, silicic acid and silica-alumina gel consisting mainly of silica are especially suitable.

Chromatography can be carried out by any desired type of procedure, such as high pressure liquid chromatography, thin-layer chromatography, or column chromatography. However, for separation on a large scale, column chromatography is preferably used. The column chromatography is carried out, for example, by using silica gel as a carrier and n-hexane, benzene, ethyl acetate, methylene chloride, or ether as a developing solvent to obtain the epimers in a pure form. Impure fractions may be repeatedly subjected to column chromatography, or fractionally crystallized to remove small amounts of impurities.

The developing speed of the 1α,24(R)-DHC is high, whereas the developing speed of its benzoyl derivative is low.

4. Second Reaction Step (synthesis of 5,7-diene derivative)

According to this invention, the 1α,24-DHC of formula (2-a) obtained by the first-step reaction is converted to a protected derivative of 1α,3β,24-trihydroxycholesta-5,7-diene after protecting the hydrogen atoms of the hydroxyl groups at the 1-, 3- and 24-positions with a protective group convertible to a hydrogen atom, or after separating the 1α,24-DHC benzoyl derivative of formula (2-b) into the 1α,24(S)-epimer and the 1α,24(R)-epimer, or after converting the benzoyl protective groups in the 1-, 3- and 24-positions of formula (2-a) to other protective groups convertible to hydroxyl groups.

Thus, according to the present invention, at least one of protected 1α,3β,24(S)-trihydroxycholesta-5,7-diene derivative and protected 1α,3β,24(R)-trihydroxycholesta-5,7-diene derivative (these will be referred to as 5,7-diene derivatives for simplicity) of the formula

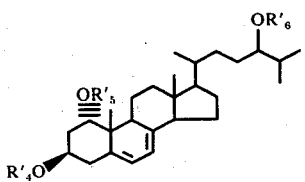
(3)

can be prepared by reacting at least one of a protected derivative of 1α,24(S)-dihydroxycholesterol dehydrobrominating a protected derivative of 1α,24(R)-dihydroxycholesterol of the following formula

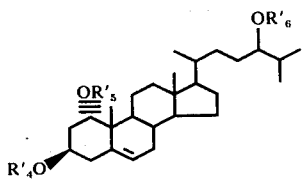
(2)

wherein $R'_4$, $R'_5$ and $R'_6$ are identical or different, and represent a protective group convertible to a hydrogen atom without changing the structure of the following formula (3),
with an allylic brominating agent in an inert organic medium, and then contacting the reaction mixture with a dehydrobrominating agent.

It is important that in the second step of forming the above 5,7-diene derivatives, the hydroxyl groups at the 1-, 3- and 24-positions of the 1α,24-DHC and its epimers of formula (2) are protected. If the second-step reaction is carried out without protecting these three hydroxyl groups of the 1α,24-DHC, the oxidation and decomposition of the hydroxyl groups cannot be prevented, and the yield of the intended 5,7-diene derivatives becomes very low.

The protective group may be any protective group capable of being converted to a hydroxyl group at its 1-, 3- and 24-positions without breaking the cholesta-5,7-diene skeleton after conversion to the 5,7-diene derivative. Examples of such protective groups are shown below.

1. Acyl groups:

$C_1$-$C_{12}$ aliphatic or aromatic carboxylic acid residues or their nitro-, halogen- and alkoxy-substituted derivatives, for example, acetyl, propanoyl, butanoyl, pentanoyl, capronyl, cyclohexanoyl, chloroacetyl, bromoacetyl, benzoy, p-bromobenzoyl, p-nitrobenzoyl, ethylbenzoyl, and toluyl groups. Of these, acetyl, benzoyl and propanoyl groups are especially preferred.

2. Groups which form ether linkages with hydroxyl groups:

A tert.-butyl group, a benzyl group, a triarylmethyl group such as a triphenylmethyl group, a tetrahydropyranyl group, a methoxymethyl group, and an alkyl-substituted silyl group such as a trimethylsilyl group. Of the above protective groups, the acyl groups (1) are especially preferred, but the invention is in no way limited to them.

The allyl-position brominating agent may be any compounds which are usually employed for the bromination of an allyl position, and for example, N-bromosuccinimide, 1,3-dibromo-5,5-dimethylhydrantoin and N-bromocaprolactam are preferably used. Usually, the amount of the allylic brominating agent is 1 to 2 equivalent times the amount of the 5-ene of formula (2).

The reaction in the present invention is first between the 1α,24-DHC of formula (2), preferably a protected 1α,24-DHC or its protected epimer, and the allylic brominating agent in an inert organic medium. Suitably, this reaction is carried out at room temperature to 140° C.

The inert organic medium is one which does not react with the brominating agent. Advantageously, it is, for example, a hydrocarbon or halogenated hydrocarbon, such as hexane, heptane, cyclohexane, ligroine, benzene, toluene, xylene, bromobenzene, chlorobenzene, nitrobenzene, carbon tetrachloride, 1,2-dichloroethane, or 1,2-bromoethane. An ether solvent, such as ethyl ether, tetrahydrofuran, dioxane, methyl cellosolve or phenyl cellosolve, can also be used. These inert organic solvents can be used either alone or in admixture.

The reaction proceeds at the above temperature. If desired, the reaction can be carried out under the irradiation of actinic light having a wavelength corresponding to infrared to ultraviolet rays. In this case, the reaction proceeds at a temperature lower than room temperature. A radical initiator, such as azobisisobutyronitrile, benzoyl peroxide or cyclohexyl hydroperoxide, can also be added in a small amount.

The dehydrobrominating agent is preferably trimethyl phosphite, s-collidine, or diethyl aniline, and they may be used in combination. Theoretically, the reaction proceeds fully when the amount of the dehydrobrominating agent is equimolar to the brominated product obtained by the previous brominating reaction, but in order to secure desirable rates of reaction and yields, the dehydrobrominating agent is used preferably in an amount of at least about 2 molar times the amount of the brominated product. Since the dehydrobrominating agent also acts as a reaction medium, there is no particular upper limit to its amount.

Usually, the reaction proceeds in good condition at a temperature of 80° to 250° C., preferably 120° to 180° C. The reaction time varies according to the type of the dehydrobrominating agent, the type of the reaction solvent, etc. For example, in a preferred embodiment wherein the reaction is carried out under reflux in a xylene-s-collidine system, the reaction is completed within a short time of about 20 minutes.

After the end of the reaction, the solvent is distilled off at reduced pressure to afford an oily crude 5,7-diene derivative.

5. Third Reaction Step (Purification of Crude 5,7-Diene Derivative)

As stated above, a method for preparing 1α-hydroxycholesterol (1α-HC) of the formula

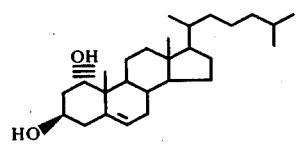
(B-5)

has already been known (D. H. R. Barton et al., J. Am. Chem. Soc., 95, 2748, 1973).

It has also been known that the above 1α-hydroxycholesterol (1α-HC) is converted to 1α,3β-diacetoxycholesta-5,7-diene of the formula

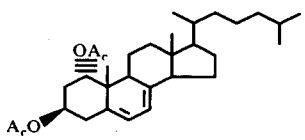

(B-6)

wherein Ac is CH₃CO-, by the same reaction as in the second step of the present invention described above, and this product is then thermally rearranged by irradiation of ultraviolet rays to convert it to 1α,3β-diacetoxycholecalciferol (vitamin D derivative) of the formula

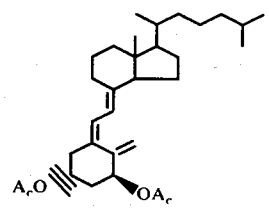

(B-1).

The inventors, therefore, attempted to thermally rearrange the 5,7-diene derivative of the formula

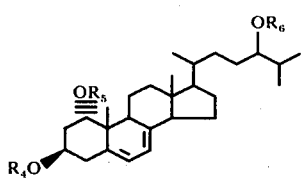

(3)

obtained in the second step by direct irradiation of ultraviolet rays by the method known in regard to the synthesis of the 1α,3β-diacetoxycholecalciferol of formula (B-1), but the desired 1α,24-dihydrocycholecalciferol derivative of the formula

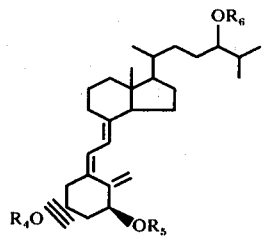

(5)

wherein $R_4$, $R_5$ and $R_6$ are the same as defined in formula (2), could not be isolated.

The inventors presumed that this is because the 5,7-diene derivative of formula (3) is impure and probably contains a 4,6-diene derivative of the formula

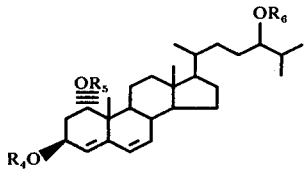

(6)

wherein $R_4$, $R_5$ and $R_6$ are the same as defined above. On this presumption, the inventors attempted to purify the crude 5,7-diene derivative formed and separated in the second step described above, by a known adsorption chromatography using silica gel as an adsorbent, that is, thin-layer chromatography or column chromatography, but none of these chromatographic methods could separate the 4,6-diene derivative of formula (6) from the crude 5,7-diene derivative of formula (3).

An example is known in which chromatography using silver nitrate was applied to the separation and purification of acetoxycholesta-5,7-dienes (Tetrahedron Letters, No. 40, 4147, 1972, and German OLS No. 2,400,931).

Thus, the inventors hit upon an idea of applying the above silver nitrate chromatography to the above crude 5,7-diene derivative of formula (3) and attempted to purify the crude 5,7-diene derivative by column chromatography using 2% silver nitrate-silica gel. But the attempt failed, and the 4,6-diene derivative could not be separated.

Various subsequent investigations about the method of purifying the crude 5,7-diene derivative finally led to the discovery that the free 5,7-diene can be separated very well from the free 4,6-diene and other impurities by a chromatographic method comprising splitting off the protective group from the crude 5,7-diene derivative of formula (3) to convert it to 1α,3β,24-trihydroxycholesta-5,7-diene (the free 5,7-diene) of the formula

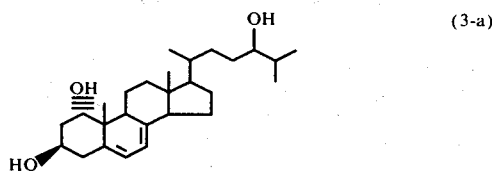

(3-a)

and bringing it into contact with a carrier containing silicon dioxide and having adsorbed thereto non-metallic silver.

This purifying process of the invention can be applied not only to the crude protected 5,7-diene derivative obtained in the second step, but also to the 5,7-diene derivative in 24(S)-epimer form or the 5,7-diene derivative in 24(R)-epimer form. In any case, it is essential that such a crude compound is subjected to the purifying process of this invention after splitting off the protective groups at the 1-, 3- and 24-positions to convert it to the free 5,7-diene of formula (3-a).

Suitable carriers containing silicon dioxide and having adsorbed thereto non-metallic silver are silica gel and silica-alumina gel containing or having adhered thereto silver nitrate. The silica gel is particularly advantageous.

Such silica gel is prepared, for example, by dissolving silver nitrate in water or a suitable organic solvent such as acetonitrile or alcohols, mixing the solution with silica gel, and then evaporating the solvent from the mixture. When it is used for column chromatography, it is activated, if desired, and filled in a glass column. When it is used for thin-layer chromatography, a suitable fixing agent, such as gips or starch is incorporated in the silica gel prepared in the above manner, and if desired, a fluorescent agent is also added to spread the mixture on a suitable plate (glass or a polyester film) in a thickness of 0.2 mm to 2 mm, fixed, and activated.

In order to impregnate silver nitrate in a thin-layer chromatographic plate made only of silica gel, the plate is immersed in a solution of silver nitrate in an organic solvent (for example, acetonitrile or an alcohol) in a suitable concentration, dried, and then activated.

The amount of silver nitrate used in the process of this invention is suitably 0.1 to 20% by weight based on silica gel, especially preferably 0.5 to 10% by weight. When the amount of silver nitrate is less than 0.1% by weight or larger than 20% by weight, the separating ability becomes poor. In the latter case, the silver nitrate is wastefully used.

Examples of a developing solvent or an eluting solvent used for thin-layer chromatography or column chromatography are organic solvents such as cyclohexane, n-hexane, benzene, toluene, chloroform, 1,2-dichloromethane, 1,2-dichloroethane, acetone, diethyl ether, tetrahydrofuran, ethyl acetate, methanol, ethanol, and propanol, and mixtures of these. Of these, mixtures of low-boiling solvents such as n-hexane, benzene, chloroform, acetone, ethyl acetate or methanol are particularly suitable. Suitable mixing ratios can be easily determined experimentally.

The methods of development, elution, and detection can be satisfactorily performed in accordance with conventional chromatographic techniques.

The inventors found as a result of applying this purifying method, the crude 5,7-diene derivative obtained in the second step contains the 4,6-diene in a weight ratio of about ½ to ¼ based on the purified 5,7-diene. Such a great quantity of the 4,6-diene can be separated and removed from the 5,7-diene substantially completely by the purifying method of this invention.

It has been found that this purifying method makes it possible to obtain the above free 5,7-diene easily in high purity and yield, and that as will be described hereinbelow, this 5,7-diene, either as such or after protecting at least one of the hydroxyl groups at its 1-, 3- and 24 positions with the same protective group as described hereinabove, can be converted to 1α,24-dihydroxycholecalciferol or its protected derivatives by irradiating ultraviolet rays and then rearranging it (isomerization).

It is believed therefore that the purifying method in the third step of the present invention is of very high commercial value.

6. Fourth step (synthesis of 1α,24-cholecalciferol or its protected derivative)

1α,24-cholecalciferol or its derivatives resulting from the protection of at least one hydroxyl group thereof with a protective group as represented by the following formula

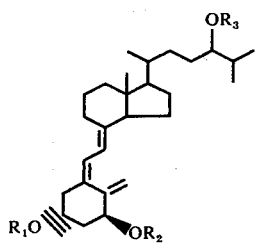

wherein $R_1$, $R_2$ and $R_3$ are the same as defined in formula (3-b), can be obtained by irradiating ultraviolet rays on at least one of the free 5,7-diene purified and separated in the third step or its derivative resulting from the protection of at least one of the hydroxyl groups at the 1-, 3- and 24-positions of the free 5,7-diene expressed by the formula

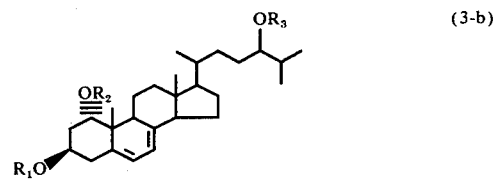

wherein $R_1$, $R_2$ and $R_3$ are identical or different and represent a hydrogen atom or a protective group convertible to a hydrogen atom without changing the structure of formula (5), in an inert organic solvent, and then isomerizing the resulting product.

The free 5,7-diene or its protected derivatives of formula (3-b) may be 1α,3β,24(S)-trihydroxycholesta-5,7-diene or its protected derivatives, or 1α,3β,24(R)-trihydroxycholesta-5,7-diene or its protected derivatives, or mixtures of these in arbitrary ratios, and they can be converted to 1α,24(S)-type, 1α,24(R)-type or mixed type dihydroxycholecalciferol or its protected derivatives by the process of the fourth step of this invention.

When $R_1$, $R_2$ and/or $R_3$ in formulae (3-b) and (5) represents a protective group, it may be the same protective group as represented by $R'_4$, $R'_5$ and/or $R'_6$ in formula (2). The purified 1α,3β,24-trihydroxycholesta-5,7-diene of formula (3-a) can be converted to its protected derivative by the same method as described hereinabove with respect to the separation of the 1α,24-DHC into the (S)- and (R)-epimers in paragraph [3] above.

In the fourth step of this invention, however, the use of a purified free 5,7-diene in which all of $R_1$, $R_2$ and $R_3$ in formula (3-b) are hydrogen atoms is more advantageous than its protected derivatives. Since 1α,24-dihydroxycholecalciferol of the following formula

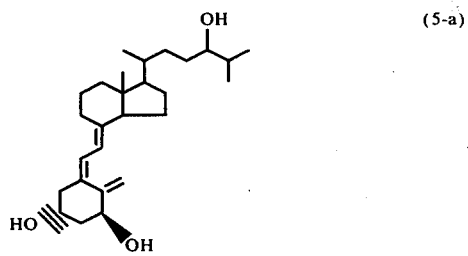

is a so-called analog of active forms of vitamin $D_3$, the use of a purified free 5,7-diene of formula (3-b) permits the direct preparation of the analog of active form of vitamin $D_3$ of formula (5-a). On the other hand, when the protected derivative of formula (3-b) is used, two extra steps of protecting the hydroxyl groups of the purified free 5,7-diene and splitting off the protective groups of the resulting protected 1α,24-dihydroxycholecalciferol. In particular, the splitting off of the protective groups involves a partial decomposition or degeneration of 1α,24-dihydroxycholecalciferol.

For this reason, too, the purifying process in the third step of this invention is a very advantageous purifying method.

The purified 5,7-diene or its protected derivatives of the formula (3-b), preferably purified free 5,7-diene, is converted to the 1α,24-dihydroxycholecalciferol or its protected derivative of formula (5) or (5-a) by first irradiating ultraviolet rays to the free purified 5,7-diene or its protected derivative in an inert organic solvent. The ultraviolet rays are those known to have a wavelength of about 200 to 360 nm, and in the present invention, those having a wavelength of 260 to 310 nm are especially preferred.

Examples of the inert organic solvent used in this step are hydrocarbons and halogenated hydrocarbonns such as hexane, heptane, cyclohexane, ligroine, benzene, toluene, xylene, bromobenzene, chlorobenzene, nitrobenzene, carbon tetrachloride, 1,2-cycloethane or 1,2-dibromoethane; ethers such as diethyl ether, tetrahydrofuran, dioxane, methyl cellosolve or phenyl cellosolve; and alcohols such as methanol, ethanol, propanol, hexanol, or cyclohexanol. Benzene, toluene, diethyl ether, methanol, and ethanol, either alone or as mixtures, are particularly preferably used in this invention. If such a solvent is used, the subsequent isomerization reaction to be described can be carried out in the same solvent after ultraviolet irradiation.

The suitable temperature for ultra-violet irradiation is −20° to 80° C., especially −10° to 20° C. Preferably, the irradiation is performed in an oxygen-free inert atmosphere such as an argon or nitrogen atmosphere.

It is believed that as a result of the ultraviolet irradiation, the 9,10-positions of 1α,3β,24-trihydroxycholesta-5,7-diene or its derivative are cleaved to yield 1α,24-dihydroxy-precholecalciferol derivative as a main product.

Isomerization of the precholecalciferol affords the 1α,24-dihydroxycholecalciferol derivative of formula (5) or (5-a).

The temperature at the time of the isomerization reaction is not essentially important for the proceeding of the reaction itself.

The 1α,24-dihydroxyprecholecalciferol derivative and the 1α,24-dihydroxycholecalciferol derivative show a certain equilibrium value which differs according to temperature, and with lower temperatures, there is a tendency to increasing proportions of the latter. However, it appears that at lower temperatures, the rate of conversion to the latter tends to become slower. Accordingly, the temperature can be determined by considering the equilibrium value and the rate of conversion. In this sense, the temperature is not essentially important for the proceeding of the reaction itself.

In actual operations, these points are considered, and isomerization temperatures of 10° to 120° C., preferably 40° to 100° C., are employed.

Desirably, the isomerization is carried out usually in an inert organic solvent. If the same preferred solvent as described above is used, it can also serve as a solvent for the isomerization reaction.

Thus, the 1α,24-dihydroxycholecalciferol or its protected derivatives of formula (5-a) or (5) is formed.

When the protective group of the protected derivative of 1α,24-dihydroxycholecalciferol is an acyl group, it can be split off by deacylation using a method which comprises decomposing it in an alkali solution of an alcohol such as methanol or ethanol, or a method which comprises reductively decomposing it with LiAlH₄, for example, in a solvent such as an ether. Preferably, the deacylation is carried out at a temperature of −10° to 50° C.

When the protective group forms an ether linkage with the hydroxyl group, a part of it can be easily removed by reduction or by contact with an acid or alkali.

Splitting off of protective groups is carried out preferably directly on the reaction mixture obtained in the fourth step.

The 1α,24-dihydroxycholecalciferol so formed can be separated and purified by column chromatography, preparative thin-layer chromatography, high speed liquid chromatography, or recrystallization. It is also possible to utilize chromatography using a carrier containing silicon dioxide having adsorbed thereto non-metallic silver as mentioned with regard to the purification of the crude 5,7-diene, for example, silica gel containing silver nitrate. Higher purity 1α,24-dihydroxycholecalciferol can be isolated by combining two or more of these purifying methods.

7. Pharmacological Activities of the Products of This Invention

The 1α,24-dihydroxycholecalciferol (1α,24-DHCC) of formula (5-a) obtained by the method of this invention described above, more specifically (i) 1α,24(S)-dihydroxycholecalciferol, (ii) 1α,24(R)-dihydroxycholecalciferol, or (iii) a mixture of the dihydroxycholecalciferols (i) and (ii) in optional ratios, is a novel compound successfully synthesized and isolated by the inventors of the present application. These compounds are vitamin D₃ analogs having superior activites, and their toxicity is low.

It has previously been known that 1α,25-dihydroxycholecalciferol (1α,25-DHCC) and 1α-hydroxycholecalciferol (1α-HCC) have superior activites as analogs of active forms of vitamin D₃. Recently, it was discovered that 1α-HCC has a very high toxicity, and its side-effects become a problem in continuous administration. No data on toxicity are available on 1α,25-DHCC, but from the various available facts, it appears that it is at least as toxic as 1α-HCC.

One purpose of the present invention is to reduce such a toxicity of the 1α-HCC. 1α,24,25-trihydroxycholecalciferol (1α,24,25-THCC) found in vivo appears to have a fairly selective, although not so strong, promoting effffect on intestinal calcium transport. If the 1α,24-DHCC epimeric mixture, 1α,24(R)-DHCC and 1α,24(S)-DHCC and 1α-24(S)-DHCC (these will be referred to generically as 1α,24-DHCC) are further metabolized in vivo, the 1α,24-DHCC is very likely to be converted to 1α,24,25-THCC. This suggests that the action of the 1α,24-DHCC epimeric mixture, 1α,24(R)-DHCC and 1α,24(S)-DHCC can be selective. The 1α,24-DHCC is a novel compound not yet found in vivo, and is fully expected to have quite a new activity.

From the above standpoint, the inventors of the present application made a comparative study on the activities of the novel compounds of this invention with regard to 1α-HCC, and found that these novel compounds in accordance with this invention, as will be shown in the following examples, have at least an equivalent effect to 1α-HCC in intestinal calcium transport, their effect on bone resorption is less than about one-third of the effect of the 1α-HCC, and that their LD₅₀ values are less than about one-tenth of that of the 1α-HCC. It has been ascertained in particular that 1α,24(S)-DHCC has a slightly weaker action of promoting intestinal calcium transport than 1α,24(R)-DHCC, but exhibits almost no bone resorption.

Accordingly, 1α,24-DHCC of this invention can be used as a unique medicine having reduced side-effects and high safety as compared with the known analogs of active forms of vitamin $D_3$ when applied, for example, to diseases induced by the abnormal metabolization of calcium. Pharmacological tests conducted by the inventors have made it clear that various optimum pharmaceutical preparations can be formed according to different diseased conditions.

As a result of the pharmacological tests, it has been found that suitable dosages of the above novel activated vitamin $D_3$ derivatives in clinical applications are 0.01 to 10 mg and preferably about 0.04 to 0.4 μg (96.2 to 962 p moles) per kilogram of the body weight.

The 1α,24-DHCC compounds of formula (5-a) are expected to be applicable to various clinical and veterinary fields, and is useful for the treatment of abnormal metabolism of calcium and phosphorus caused by liver failure, renal failure, gastrointestinal tract failure, and parathyroid failure, and related bone diseases, such as vitamin D-dependent rickets, renal osteodystrophy, hypoparathyroidism, osteoporosis, osteomalacia, Peget's disease, malabsorption syndrome, hypocalcemia induced by liver cirrhosis, hypocalcemia induced by steatorrhoea, hypocalcemia caused by vitamin D-resistant rickets. These compounds are expected to be safer medicines than the known 1α-HCC and 1α-DHCC. It is also possible to use a composition containing at least one of 1α,24(R)-DHCC and 1α,24(S)-DHCC together with other calcium metabolism regulating agents. For example, it can be applied to the treatment of Paget's disease in combination with calcitonin.

Suitable routes of administration include oral, buccal and parenteral (intramuscular, subcutaneous, intravenous, and rectal). Dosage forms are, for example, compressed tablets, coated tablets, hard or soft elastic gelatin capsules, ethyl alcohol solutions, oil solutions, and aqueous suspensions.

The solvent for the oil solutions may be a vegetable oil such as a corn, cotton seed, coconut, almond or peanut oil, a fish liver oil, or an oily ester such as Polysorbate 80.

For rectal administration, the compounds in accordance with this invention may be formed into a pharmaceutical composition containing a suppository base such as cacao oil or other triglycerides. In order to prolong the life of storage, the composition advantageously includes an anti-oxidant such as ascorbic acid, butylated hydroxyanisole or hydroquinone.

Feed compositions for domestic animals which contain the 1α,24-DHCC of this invention can be used in amounts not causing toxicity for the prevention of hypocalcemia of cows at the time of delivery or near the time of delivery, or the prevention of hypocalcemia of domestic animals with no history of hypocalcemia. When these compounds are administered to poultry during ovide-position, it is possible to prevent them from laying soft-shelled eggs. This constitutes another characteristic of the 1α,24-DHCC of this invention.

The following Examples illustrate the present invention more specifically.

The test methods used in these Examples for the determination of the characteristics of the final products were as follows:

Unless otherwise specified, NMR spectra were determined by Varian EM 360 or JEOL PS/PFT-100 (Nippon Electronics Co., Ltd.) in deuterochloroform ($CDCl_3$) using tetramethylsilane as internal standard.

Mass spectra and high resolution mass spectra were determined by using Shimadzu LKB-9000 (trademark for a product of Shimazu Seisakusho Co., Ltd.).

UV spectra were determined by Hitachi EPS-3T (trademark for a product of Hitachi Limited) using an ethanol solution.

The melting point was measured by means of a hot stage microscope, and the resulting values were not corrected.

The absolute configuration of 1α,24-dihydroxycholesterol was determined as follows:

An epimeric mixture of 24,24-epoxycholesterol 3-benzoate, that is, a mixture of

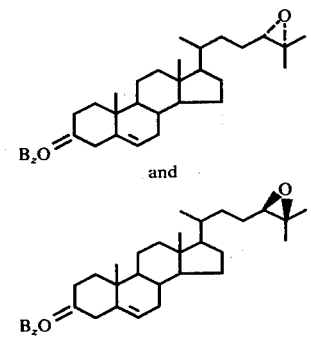

wherein $B_z$ represents a benzoyl group, is chromatographed using silica gel as a carrier to separate and recover the two epimers. Each of the epimers is methanolyzed to form a 24-OH derivative and a 25-$OCH_3$ derivative. The method for determining the absolute configuration of the two epimers by applying the modified Horean's Method, which is disclosed in Tetrahedron Letters 1 15, 1975, was utilized. By reducing the two epimers whose absolute configuration has thus been determined with an $AlCl_3$-$LiAlH_4$ system, a 24(R)-hydroxy derivative is obtained from the 24(R),25-epoxy derivative, and a 24(S)-hydroxy derivative is obtained from the 24(S),25-epoxy derivative. Since it is known that the latter S-derivative is more polar than the former R-derivative, it is assumed that this fact is applicable also to 1α,24-dihydroxycholesterol. Thus, this 1α,24-dihydroxycholesterol is converted to its tribenzoate- or dibenzoate-derivative which is then chromatographed through a silica gel column. Thus, a more polar epimer is converted to a 1α,24(S)-derivative and a less polar epimer, to a 1α,24-(R)-derivative.

Where in the present application, there is no specific reference to an R-derivative or an S-derivative, for example, when reference is merely to 1α,24-DHCC, it represents an equimolar mixture of 1α,24(R)-DHCC and 1α,24(S)-DHCC.

EXAMPLE 1

A. Synthesis of Starting Material

1α,2α-epoxy-24-ketocholesta-4,6-dien-3-one was prepared by the following three steps (1) to (3).

1. Synthesis of 24-ketocholesterol from fucosterol

Fucosterol (4.1 g) was dissolved in 100 ml. of methylene chloride, and while cooling the solution with dry ice-acetone to about −20° C., the fucosterol was oxidized for 30 minutes with ozone at a rate of generation of 0.86 g/hr and in a concentration of 17.2 $g/m^3$ ($O_2$). After the reaction, 8 g of zinc powder and 200 ml. of acetic acid were added, and the resulting ozonide was reductively decomposed at room temperature for 24 hours. The resulting zinc acetate was separated by filtration, and washed with an aqueous solution of sodium carbonate. The methylene chloride phase separated was thoroughly washed with water, and dried with anhydrous sodium sulfate. The methylene chloride was evaporated off at reduced pressure, and the resulting white crystals were column-chromatographed using silica gel as a carrier (eluted with a benzene-n-hexane mixed solvent) to afford 2.8 g of 24-ketocholesterol in a yield of 70.3%.

2. Synthesis of 24-ketocholesta-1,4,6-trien-3-one from 24-ketocholesterol 4.0 g of 24-ketocholesterol and 7.0 g of 2,3-dichloro-5,6-dicyanobenzoquinone were dissolved in 140 ml. of dioxane, and the solution was stirred under reflux of dioxane for 27 hours. After the reaction, the reaction mixture was cooled to room temperature. The resulting hydroquinone derivative was separated by filtration, and washed with 30 ml. of dioxane. The filtrate and the wash liquid were combined, and dioxane was evaporated off at reduced pressure to afford a black-brown oily substance.

The oily substance was separated and purified by column chromatography using alumina as a carrier (eluted with a methylene chloride-acetone mixed solvent) to afford 2.76 g of 24-ketocholesta-1,4,6-trien-3-one as crystals. Analaysis of the product showed the following results. NMR spectrum:
  0.86 (3H, s, C-18-$CH_3$),
  1.20 (3H, s, C-19-$CH_3$),
  1.15 (6H, d, J=10 Hz, C-26,27-$CH_3$),
  5.95 - 6.10 (3H, m, C-4, 6, 7-H),
  6.29 (1H, dd, J=11, 15Hz, C-2-H),
  7.10 (1H, J=11 Hz, C-1-H)
Molecular weight (by gas mass spectrum):
  394 ($M^+$)

3. Synthesis of 1α,2α-epoxy-24-ketocholesta-4,6-dien-3-one from 24-ketocholesta-1,4,6-trien-3-one 3.53 g of 24-ketocholesta-1,4,6-trien-3-one was dissolved in a mixture of 100 ml. of methanol, 20 ml. of tetrahydrofuran and 50 ml. of dioxane, and 1.6 ml. of a 5% by weight methanol solution of sodium hydroxide and 5 ml. of 30% aqueous hydrogen peroxide were added. The reaction was carried out at room temperature for 24 hours. After the reaction, a small amount of acetic acid was added to neutralize the solution to a pH of 7. The reaction mixture was then extracted by adding water and ether. The ethereal phase was thoroughly washed with water, and dried with anhydrous sodium sulfate. The ether was evaporated off at reduced pressure to afford 4.04 g of a light yellow solid. The solid product was column-chromatographed using silica gel (eluted with a benzene-ether mixed solvent) to afford 2.52 g of 1α,2α-epoxy-24-ketocholesta-4,6-dien-3-one which showed the following characteristics.
Melting point: 150° to 151.5° C.
UV spectrum: $\lambda_{max}$ ethanol 291 nm
High resolution mass spectrum:
  Found=410.2793
  Require ($M^+$)=410.2821 ($C_{27}H_{38}O_3$)
NMR spectrum:
  0.80 (3H, s, C-18-Hs),
  1.15 (3H, s, C-19-Hs),
  3.43 (1H, dd, J=4Hz, J=1.5Hz, C-2-H)
  3.60 (1H, d, J=4Hz, C-1-H),
  5.68 (1H, d, J=1.5Hz, C-4-H)
  6.10 (2H, s, C-6, C-7-Hs)

B. Synthesis of 1α,24-dihydroxycholesterol of This Invention (The First Step)

Liquid ammonia (10 ml.) dried with metallic sodium was trapped in a three-necked flask equipped with a dropping funnel and a dry ice cooler while cooling the flask with a cooling medium consisting of acetone and dry ice. Metallic lithium (150 mg) was added to the liquid ammonia, and they were stirred for 10 minutes. The mixture was dissolved in 15 ml. of tetrahydrofuran, and 100 mg of 1α,2α-epoxy-24-ketocholesta-4,6-dien-3-one was added dropwise in the course of 10 minutes.

After the addition, the flask was separated from the cooling medium, and ammonia was refluxed for 20 minutes. Again, the flask was immersed in the cooling medium, and 1.5 g of a fully dried powder of ammonium chloride was added slowly over the course of 2 hours. The flask was withdrawn from the cooling medium, and the reaction was continued with stirring.

Stirring was stopped when the blue color of the solution completely disappeared. The cooler was removed from the flask, and nitrogen gas was introduced to remove the ammonia.

Ethyl acetate (60 ml.) and 60 ml. of 1N-hydrochloric acid were added to the residue to subject it to distributive extraction. The ethyl acetate phase separated was thoroughly washed with water, and dried, followed by evaporating off the ethyl acetate at reduced pressure. The residue was dissolved in 3 ml. of ethyl acetate, and chromatographed through a column containing silica gel as a carrier using an eluting solvent consisting of a mixture of benzene and acetone. There was obtained 61 mg of a purified product having the following characteristics.
NMR spectrum (in $C_5D_5H$), δ (ppm):
  0.70 (3H, s, 18-$CH_3$),
  0.99 (3H, s, 19-$CH_3$),
  3.28 (4H, m, 24-H and hydroxy H),
  3.82 (1H, m, 1β-H),
  4.00 (1H, m, 3α-H),
  5.50 (1H, m, 6-H)
Mass spectrum (see FIG. 1):
  418 ($M^+$), 400, 382
High resolution mass spectrum:
  Found = 418.3428
  Require, $M^+(C_{27}H_{46}O_3)$ = 418.3449
From the above characteristics, the resulting product was identified as 1α,24-dihydroxycholesterol.

EXAMPLE 2

Synthesis of 1α,24-dihydroxycholesterol (First Step)

Liquid ammonia (15 ml.) dried with metallic sodium was trapped in a three-necked flask equipped with a dropping funnel and a dry ice cooler while cooling the flask with a cooling medium consisting of acetone and dry ice. Then, 400 mg of metallic sodium was added to it, and they were stirred for 10 minutes. The mixture was then dissolved in 18 ml. of tetrahydrofuran, and 100 mg of 1α,2α-epoxy-24-ketocholesta-4,6-dien-3-one was added dropwise over the course of 10 minutes.

After the addition, 1.8 g of a powder of ammonium chloride was added over the course of 1 hour in the same way as in Example 1. The reaction mixture was treated in the same way as in Example 1, and 69 mg (yield 68%) of a product which showed the same NMR spectrum, mass spectrum and high resolution mass spectrum as in Example 1 was obtained. This product was identified as 1α,2α-24-dihydroxycholesterol.

EXAMPLE 3

A. Synthesis of 1α,24-dihydroxycholesterol tribenzoate 1.25 g of 1α,24-dihydroxycholesterol was mixed with 1.55 g of benzoyl chloride and 20 ml. of pyridine, and they were reacted at 40° C. for one day. Water (5 ml.) was added to the reaction mixture, and it was extracted with 50 ml. of diethyl ether. The ethereal phase was washed with an acid and then with an alkali, dried, and evaporated to remove the ether to afford crude 1α,3β,24-tribenzoyloxycholest-5-ene.

B. Separation of 24(R)-derivative and 24(S)-derivative of 1α,3β,24-tribenzoyloxycholest-5-ene An n-hexane solution of 1.58 g of the crude 1α,3β,24-tribenzoyloxycholest-5-ene was chromatographed through a column containing 100 g of silica gel as a carrier to divide it into fractions each having a volume of 50 ml. The purity of each of the fractions was ascertained by high pressure liquid chromatography, and the corresponding fractions were combined and the solvent was evaporated off. Two epimers having the following NMR spectra were obtained. A less polar epimer (500 mg) eluted at an early stage was the 24(R)-derivative, and a more polar epimer (490 mg) eluted at a stage toward the end was the 24(S)derivative.

NMR spectra of 1α,3β,24(R)-tribenzoyloxycholest-5-ene:
0.65 (3H, s, C-18),
0.92 (3H, s, C-21),
1.01 (6H, b, s, C-25, 26),
1.20 (3H, s, C-19),
5.00 (1H, m, C-24),
5.20 (1H, m, C-3),
5.44 (1H, m, C-1),
5.70 (1H, m, C-6),
7.5 (9H, m, benzoyl),
8.1 (6H, m, benzoyl)

NMR spectrum of 1α,3β,24(S)-tribenzoyloxycholest-5-ene:
0.63 (3H, s, C-18)
Other spectrum data are the same as those of the 24(R)-derivative.

EXAMPLE 4

A. Synthesis of 1α,24-dihydroxycholesterol dibenzoate 2.5 g of 1α,24-dihydroxycholesterol was mixed with 2.10 g of benzoyl chloride and 40 ml. of pyridine, and the mixture was allowed to stand for one day at 20° C.

The reaction mixture was treated in the same way as in Example 3 (a) to obtain crude 1α-hydroxy-3β,24-dibenzoyloxycholest-5-ene.

B. Separation of 24(R)-derivative and 24(S)-derivative of 1α-hydroxy-3β,24-dibenzoyloxycholest-5-ene 2.1 g of the crude 1α-hydroxy-3β,24-dibenzoyloxycholest-5-ene was chromatographed through a column containing 30 g of silica gel using an eluting solvent consisting of a 200:1 mixture of benzene and ethyl acetate to divide it into fractions each having a volume of 50 ml. Each of the fractions was subjected to high pressure liquid chromatography to ascertain their purity. The corresponding fractions were combined, and the solvent was evaporated off to form two epimers having the following NMR spectrum data.

A less polar epimer (500 mg, melting point 168°–169° C.) was the 24(R)-derivative, and a more polar epimer (600 mg, melting point 139.5°–140.5° C.) was the 24(S)-derivative.

NMR spectrum of 1α,hydroxy-3β,24(R)-dibenzoyloxycholest-5-ene:
0.67 (3H, s, C-18)
0.96 (6H, b, s, C-19,21),
1.00 (6H, d, J = 6Hz, C-25,26),
3.96 (1H, m, C-1),
5.06 (1H, m, C-24),
5.36 (1H, m, C-3),
5.71 (1H, m, C-6),
7.52 (6H, m, benzoyl),
8.12 (4H, m, benzoyl)

NMR spectrum of 1α-hydroxy-3β,24(S)-dibenzoyloxycholest-5-ene:
0.70 (3H, s, C-18)
Other spectrum data are the same as those of the 24(S)-derivative.

EXAMPLE 5

A. Synthesis of 1α,3β,24-triacetoxycholest-5-ene 300 mg of 1α,24-dihydroxycholestrol was reacted with 40 ml. of acetic anhydride and 125 ml. of pyridine for 3 hours at 95° C. The reaction mixture was treated in the same way as in Example 3, (A) to afford crude 1α,3β,24-triacetoxycholest-5-ene. The crude product was chromotographed through a column containing silica gel as a carrier using an eluting solvent consisting of benzene to afford 325 mg of purified 1α,3β,24-triacetoxycholest-5-ene as an oily purified product having the following NMR spectrum and mass sepctrum.

NMR spectrum:
0.67 (3H, s, C-18),
2.02 (9H, s, 3-acetyl),
4.8 (2H, m, 3α and 24-$H_2$),
5.05 (1H, m, 1β-H),
5.65 (1H, m, 6-H), Mass spectrum:
484 ($M^+$-$CH_3COOH$), 424, 364

B. Synthesis of 1α,3β,24-triacetoxycholesta-5,7-diene (Second Step)

300 mg of 1α,3β,24-triacetoxycholest-5-ene was reacted with 90 mg of 1,3-dibromo-5,5-dimethylhydantoin in 4.5 ml. of n-hexane under reflux for 15 minutes. The reaction mixture was cooled, and the resulting 5,5-dimethylhydantoin and the excessive 1,3-dibromo-5,5-dimethylhydratoin were removed by filtration. The filtrate was concentrated at reduced pressure to afford 349 mg of a yellow oily substance. Xylene (2.5 ml.) was added to this substance to form a solution. The resulting solution was added dropwise over the course of 15 minutes to a solution held at 165° C. of 0.85 ml. of s-collidine in 1.9 ml. of xylene, and the reaction was carried out for an additional 10 minutes. After the reaction, the hydrobromide of s-collidine was removed by filtration, and the s-collidine and xylene were evaporated off at reduced pressure. The residue was dissolved in diethyl ether. The ethereal phase was washed with 1N-hydrochloric acid and a 5% aqueous solution of sodium bicarbonate, and repeatedly with water. It was then treated with activated carbon, and the ether was evaporated off at reduced pressure to afford 310 mg of a yellow oily substance. This oily substance was carefully separated twice by column chromatography (elution with benzene) using silicic acid to afford 69 mg (yield 23%) of a non-crystalline purified product. From the following spectrum data, this product was identified as 1α,3β,24-triacetoxycholesta-5,7-diene.
UV spectrum, $\lambda_{max}^{ethanol}$ (nm):
 262, 271, 282, 294
NMR spectrum:
 2.02 and 2.04 (9H, s, CH$_3$COO-),
 4.75 (2H, b, 3α- and 24-H),
 5.01 (1H, b, 1β-H),
 5.35 (1H, d, J=5.5Hz, 6 or 7-H),
 5.69 (1H, d, I = 5.5Hz, 6 or 7-H)
Mass spectrum:
 542 (M$^+$), 514, 482, 422, 362, 249, 204

EXAMPLE 6

Synthesis of 1α,3β,24-triacetoxycholesta-5,7-diene (Second Step)

150 mg of 1α,3β,24-triacetoxycholest-5-ene was reacted with 45 mg of 1,3-dibromo-5,5-dimethylhydantoine in 3 ml. of n-hexane for 15 minutes under reflux. The reaction mixture was cooled, and the resulting crystals were removed by filtration. The filtrate was concentrated at reduced pressure to afford a yellow oily substance. To this substance was added 1.3 ml. of xylene. The resulting solution was added dropwise over the course of about 15 minutes to a solution of 0.25 ml. of trimethylphosphite in 4 ml. of xylene under reflux, and the reaction was performed for an additional 90 minutes. The reaction mixture was then concentrated at a temperature of less than 75° C. to afford 148 mg of an oily substance. This substance was treated in the same way as in Example 5, (B). The final product showed the same UV, mass, and NMR spectrum data as the 1α,3β,24-triacetoxycholesta-5,7-diene obtained in Example 5, (B).

EXAMPLE 7

Synthesis of 1α,3β,24-tribenzoyloxy-cholesta-5,7-diene (Second Step)

200 mg of 1α,3β,24-tribenzoyloxy-cholest-5-ene prepared in the same way as in Example 5, (A) was heated for 15 minutes under reflux together with 55 mg of N-bromosuccinimide in 15 ml of carbon tetrachloride. The reaction mixture was cooled, and the resulting crystals were removed by filtration. The filtrate was concentrated, and 5 ml. of xylene was added to the residue to form a solution.

The resulting solution was added dropwise over the course of 15 minutes to a solution of 0.2 ml. of trimethyl phosphite in 4 ml. of xylene under reflux, and the mixture was further refluxed for 90 minutes.

The reaction mixture was then concentrated at a temperature of less than 75° C., and the residue was carefully chromatographed twice through a column containing silicic acid using benzene as an eluting solvent to afford 50 mg (yield 25%) of a purified non-crystalline product. This product showed the following spectra, and was identified as 1α,3β,24-tribenzoyloxy-cholesta-5,7-diene.
UV spectrum, s$\lambda_{max}^{ethanol}$ (n m):
 231, 262, 271, 282, 294
NMR spectrum:
 4.95 (2H, b, 3α-H and 24-H),
 5.32 (2H, b, 1β-H and 6 or 7-H),
 5.72 (1H, d, J = 6Hz, 6 or 7H),
 7.49 and 8.02 (15H, m, aromatic H)
Mass spectrum:
 728 (M$^+$), 638, 620, 606, 484, 362.

EXAMPLE 8

Synthesis of 1α,3β,24(S)-triacetoxycholesta-5,7-diene (Second Step)

1α-Hydroxy-3β,24(S)-dibenzoyloxy-cholest-5-ene prepared in the same way as in Example 4, (B) was reduced with LiAlH$_4$ in dry diethyl ether to form 1α,3β,24(S)-trihydroxy cholest-5-ene. This product (180 mg) was then reacted with 24 ml. of acetic anhydride and 75 ml. of pyridine at 95° C. for 3.5 hours. The product was treated in the same way as in Example 3, (A), and chromatographed through a column containing silica gel as a carrier to afford 195 mg of 1α,3β,24(S)-triacetoxy-cholest-5-ene.

150 mg of this product was purified in the same way as in Example 5 to afford 43.5 mg (yield 29%) of a purified product having the following spectrum data. This purified product was identified as 1α,3β,24(S)-triacetoxycholesta-5,7-diene.
UV spectrum, $\lambda_{max}^{ethanol}$ (nm):
 262, 271, 282, 294
NMR spectrum:
 2.02 and 2.04 (9H, s, CH$_3$COO-),
 4.75 (2H, b, c-3-, C-24-H),
 5.01 (1H, b, c-1-H),
 5.35 (1H, d, J = 5-6Hz, C-6 or C-7-H),
 5.69 (1H, d, J = 5-6Hz, C-6 or C-7-H)
Mass spectrum:
 542 (M$^+$), 514, 482, 422, 362, 249, 209

EXAMPLE 9

Synthesis of 1α,3β,24(S)-tribenzoyloxy-cholesta-5,7-diene (Second (Step)

100 mg of 1α,3β,24(S)-tribenzoyloxy-cholest-5-ene obtained in the same way as in Example 3, (B) was heated under reflux for 15 minutes together with 23 mg of 1,3-dibromo-5,5-dimethylhydantoine in 16 ml. of carbon tetrachloride. The reaction mixture was cooled, and the resulting crystals were removed by filtration. The filtrate was concentrated and 2.5 ml. of xylene was added to the residue. The solution was added dropwise over the course of 15 minutes to a solution under reflux of 0.3 ml. of s-collidine in 2 ml. of xylene, and further refluxed for 10 minutes.

After the reaction, the hydrobromide of s-collidine was removed by filtration, and s-collidine and xylene were evaporated off at reduced pressure. The residue was dissolved in diethyl ether. The ethereal phase was washed with 1N-hydrochloric acid and a 5% aqueous solution of sodium bicarbonate, and then repeatedly with water. The ethereal phase was then dried, and the ether was evaporated off at reduced pressure to afford a yellow oily substance.

The oily substance was carefully chromatographed twice through a column containing silicic acid using benzene as an eluting solution to afford 28 mg (yield 28%) of a purified noncrystalline product. This product had the following spectra, and was identified as 1α,3β,24(S)-tribenzoyloxycholesta-5,7-diene.
UV spectrum, $\lambda_{max}^{ethanol}$ (nm):

231, 262, 271, 282, 294
NMR spectrum:
4.95 (2H, b, C-3 and C-24-Hs),
5.32 (2H, b, C-1 and C-6 or C-7-H),
5.72 (1H, d, J = 6Hz, C-6 or C-7-H),
7.49 and 8.02 (15H, m, aromatic Hs),
Mass spectrum:
728 (M$^+$), 638, 620, 606, 484, 362

EXAMPLE 10

Synthesis of
1α-acetoxy-3β-24(S)-dibenzoyloxy-cholesta-5,7-diene
(Second Step)

1α-Hydroxy-3β,24(S)-dibenzoyloxy-cholest-5-ene prepared and separated in the same way as in Example 4, (B) was reacted with acetic anhydride and pyridine in the same way as in Example 5, (A). The reaction product was purified in the same way as in Example 5 to afford 1α-acetoxy-3β,24(S)-dibenzoyloxy-cholest-5-ene.

462 mg of 1α, acetoxy-3β,24(S)-dibenzoyloxycholest-5-ene was reacted with 188.6 mg of N-bromosuccinimide in 16 ml. of carbon tetrachloride under reflux for 30 minutes. The reaction mixture was cooled, and the resulting crystals were removed by filtration. The filtrate was concentrated at reduced pressure to afford a yellow oily substance. To the substance was added 6.8 ml. of xylene to form a solution. The solution was added dropwise to a solution under reflux of 0.4 ml. of trimethyl phosphite in 8 ml. of xylene, and the reaction was carried out for an additional 90 minutes. After the reaction, the reaction mixture was concentrated at reduced pressure to afford an oily product. This product showed the following spectra, and was identified as 1α-acetoxy-3β,24(S)-dibenzoyloxy-cholesta-5,7-diene.
UV spectrum, $\lambda_{max}^{ethanol}$ (nm):
231, 262, 271, 282, 294
NMR spectrum:
2.04 (3H, s, CH$_3$COO-),
4.7–5.4 (3H, m, 1β,3α and 24-H$_3$),
5.33 (1H, d, J = 6Hz, 6 or 7-H),
5.70 (1H, d, J = 6Hz, 6 or 7-H),
7.4–8.2 (10H, m, aromatic Hs)

EXAMPLE 11

Synthesis of
1α,3β,24(R)-triacetoxy-cholesta-5,7-diene (Second Step)

1α-Hydroxy-3β,24(R)-dibenzoyloxy-cholest-5-ene prepared and separated in the same way as in Example 4, (B) was subjected to the same procedure as in Example 8. A purified product having quite the same UV, NMR and mass spectra as the corresponding S-epimer obtained in Example 8 was formed in a yield of 28%. This product was identified as 1α,3β,24(R)-triacetoxy-cholesta-5,7-diene.

EXAMPLE 12

Synthesis of
1α,3β,24(R)-tribenzoyloxy-cholesta-5,7-diene
(Second Step)

1α,3β,24(R)-tribenzoyloxy-cholest-5-ene prepared and separated in the same way as in Example 3, (B) was subjected to the same procedure as in Example 9.

A purified product having quite the same UV, NMR, and mass spectra as the corresponding S-epimer obtained in Example 9 was obtained in a yield of 27%.

This product was identified as 1α,3β,24(R)-tribenzoyloxy-cholesta-5-diene.

EXAMPLE 13

Synthesis of
1α-acetoxy-3β,24(R)-dibenzoyloxy-cholesta-5,7-diene
(Second Step)

1α-Hydroxy-3β,24(R)-dibenzoyloxy-cholest-5-ene prepared and separated in the same way as in Example 4, (B) was subjected to the same procedure as in Example 10.

A purified product having quite the same UV and mass spectra as the corresponding S-epimer obtained in Example 10 was formed. This product was identified as 1α-acetoxy-3β,24(R)-dibenzoyloxy-cholesta-5,7-diene.

EXAMPLE 14

A. Synthesis of 1α,3β,24-triacetoxy-cholesta-5,7-diene from 1α,3β,24-triacetoxy-cholest-5-ene In accordance with the procedure of Example 5, (B), 1α,3β,24-triacetoxy-cholest-5-ene was reacted with 1,3-dibromo-5,5-dimethylhydantoin and s-collidine in n-hexane. The reaction product was washed with acid and alkali in ether, and treated with activated carbon to afford a crude reaction mixture containing 1α,3β,24-triacetoxy-cholesta-5,7-diene.

B. Hydrolysis of
1α,3β,24-triacetoxy-cholesta-5,7-diene

The crude product obtained in (A) above was hyrolyzed in a 5% methanol solution of potassium hydroxide to afford a crude reaction mixture containing 1α,3β,24-trihydroxycholesta-5,7-diene.

C. Determination of the purity of
1α,3β,24-trihydroxycholesta-5,7-diene

The UV spectrum of 100% pure 1α,3β,24-trihydroxycholesta-5,7-diene is $\lambda_{max}^{ethanol} = 282$ nm, and the UV spectrum of 100% pure 1α,3β,24-trihydroxy-4,6-diene is $\lambda_{max}^{ethanol} = 240$ nm. Our investigations have shown that the mixing ratio between these two compounds can be determined by comparing their $\lambda_{max}$ values.

The ratio of the 5,7-diene derivative and the 4,6-diene derivative in the crude reaction mixture obtained in (B) above was determined by this procedure, and it was found that the molar ratio of 1α,3β,24-trihydroxycholesta-5,7-diene to 1α,3β,24-trihydroxycholesta-4,6-diene was about 3:1.

D. Separation of
1α,3β,24-trihydroxycholesta-5,7-diene and
1α,3β,24-trihydroxy-cholesta-4,6-diene (Third Step)

(D-1). Separation by preparative thin-layer chromatography

A commercially available plate for preparative thin-layer chromatography (silica gel, a product of Merck Company, 20 cm × 20 cm × 0.5 mm) was immersed in a solution of silver nitrate in acetonitrile to impregnate it in an amount of about 1.5% by weight as silver nitrate, and heat-treated at 70° C. for 2 hours. The chromatographic plate so obtained was used for the subsequent separating operation.

The crude reaction mixture (30 mg) obtained in (B) above was adsorbed to the plate and developed through about 20 cm with a 6% methanol-chloroform mixed solvent. After air drying the plate, the reaction mixture was again developed with the same solvent. It showed two bands at an RF of about 0.23 and about 0.33. These fractions were scraped off, and extracted with ethyl acetate from the silica gel. There were obtained 17.1 mg (57%) of a white solid substance (Rf = 0.23), and 6.0 mg (20%) of a white solid substance (Rf =0.33).

A part of the plate was colored using sulfuric acid, and a band of Rf =about 0.38 was confirmed. This fraction was scraped off, and extracted in the same way as above to afford about 1 mg of a solid substance.

These products had the following spectra. The product with an Rf of 0.23 was identified as $1\alpha,3\beta,24$-trihydroxy-cholesta-5,7-diene; the product with an Rf of 0.33, as $1\alpha,3\beta,24$-trihydroxycholesta-4,6-diene; and the product with an Rf of 0.38, as $1\alpha,24$-dihydroxycholesterol.

1. Product with Rf =0.23 ($1\alpha,3\beta,24$-trihydroxy-cholesta-5,7-diene)

Figure 2:
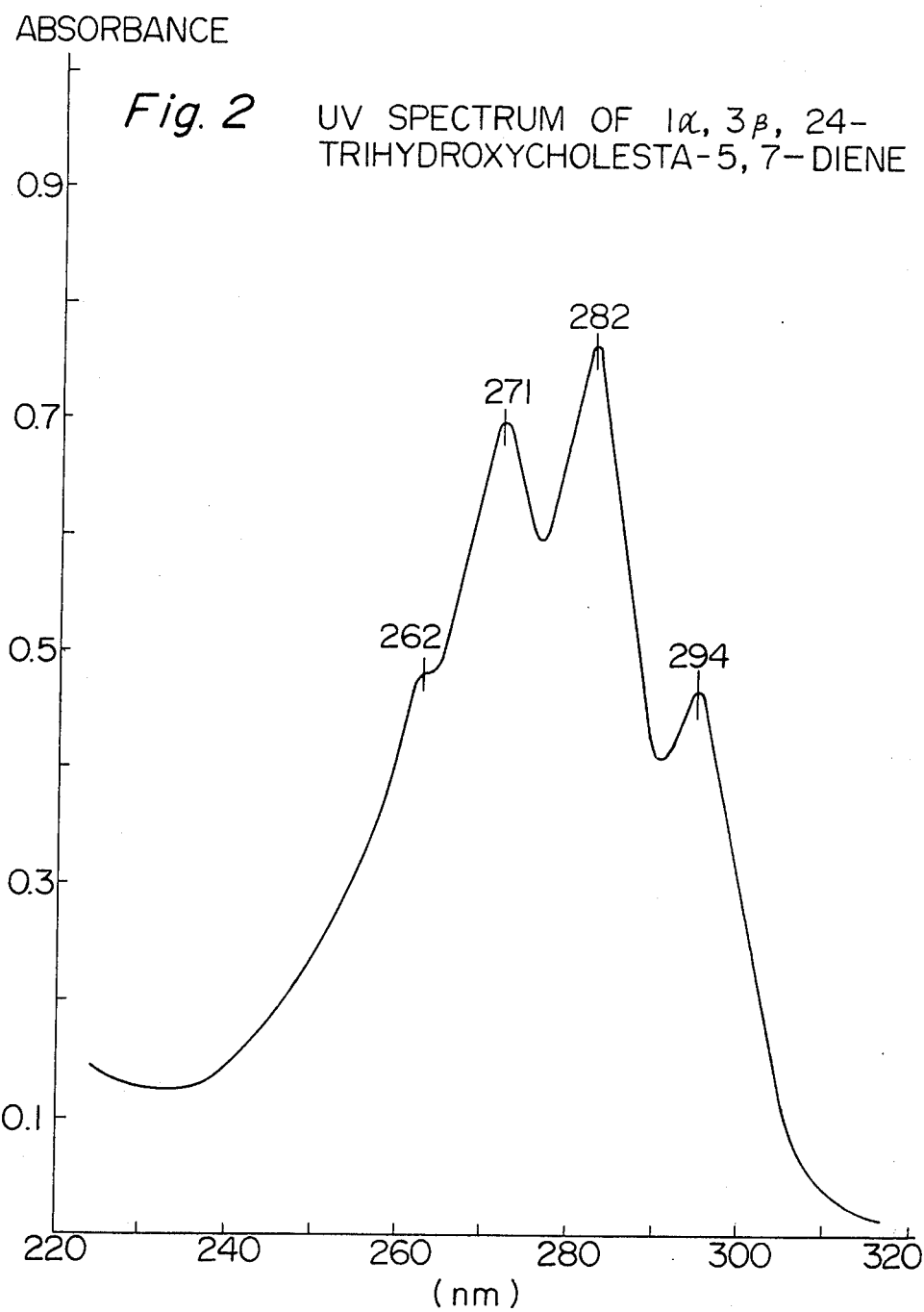

UV spectrum (see FIG. 2), $\lambda_{max}^{ethanol}$ (nm):
262, 271 ($\epsilon = 11,000$), 282 ($\epsilon = 12,000$), 294 ($\epsilon = 7000$)

NMR spectrum (in $C_3D_6O$):
0.63 (3H, s, 18-$CH_3$),
3.30 (1H, m, 24-H),
3.70 (1H, m, 1$\beta$-H),
4.08 (1H, m, 3$\alpha$-H),
5.30 (1H, d, J = 6Hz, 6 or 7-H),
5.60 (1H, d, J = 6Hz, 6 or 7H), Mass spectrum (see FIG. 3):
416 ($M^+$), 398, 380, 357, 251, 227, 197, 157

Melting point (°C.):
102° to 103° C.

2. Product with Rf = 0.33 ($1\alpha,3\beta,24$-trihydroxy-cholesta-4,6-diene)

UV spectrum, $\lambda_{max}^{ethanol}$ (nm):
233, 240, 248

Mass spectrum:
416 ($M^+$), 398, 380

3. Product with Rf = 0.38 ($1\alpha,24$-dihdyroxycholesterol)

This corresponded with a standard sample with Rf = 0.38.

D-2 Separation by column chromatography

Silica gel commerically available for use in column chromatography (C-200, trademark for a product of Wako Jyunyaku Kogyo Kabushiki Kaisha) was impregnated with about 2% by weight of silver nitrate while using it as a solution, and heat-treated at 70° C. for 2 hours. The silica gel was then packed in a glass column with a diameter of 1 cm and a length of 30 cm. 40 mg of the crude reaction mixture obtained in (B) above was poured into the column, and eluted with a mixed solvent consisting of benzene and ethyl acetate. It was divided into fractions each with a volume of about 20 ml. These fractions were separated while monitoring by thin-layer chromatography and UV spectrum.

When the volume ratio of benzene to ethyl acetate was 2:1 to 1:1, 7.6 mg (yield 19%) of a product corresponding to Rf=0.33 in (D-1) was obtained. When this ratio was 1:1, 19.6 mg (49%) of a product corresponding to Rf = 0.23 was obtained.

These products were identified by various spectrum data.

COMPARATIVE EXAMPLE 1

This Example illustrates the separation of $1\alpha,3\beta,24$-trihydroxy-cholesta-5,7-diene and $1\alpha,3\beta,24$-trihydroxy-cholesta 4,6-diene by a carrier containing silicon dioxide but not containing non-metallic silver (comparison with regard to the third step).

30 mg of a mixture of $1\alpha,3\beta,24$-trihydroxy-cholesta-5,7-diene and $1\alpha,3\beta,24$-trihydroxy-cholesta-4,6-diene in a molar ratio of 3:1, which had been prepared in the same way as in Example 14, (A) and (B) and identified in the same way as in Example 14, (C), was chromatographed through a column with a diameter of 1 cm and a length of 30 cm using silica gel as a carrier in an attempt to separate it into the constituents.

A mixed solvent of benzene and ethyl acetate was used as a developing solvent in varying mixing volume ratios from 10:1 to 1:1, and the starting mixture was divided into fractions each with a volume of about 20 ml. The separation was attempted while monitoring by thin-layer chromatography and UV spectrum. When the mixing ratio of benzene to ethyl acetate was about 2:1, the main component began to flow out. Analysis of each of these fractions by UV spectrum showed that in all of the fractions analyzed, an absorption was observed at 283, 240, 248, 262, 271, 282, and 294 nm. As a result, it was found that when silica gel was used as a carrier, the $1\alpha,3\beta,24$-trihydroxy-cholesta-5,7-diene could not be separated from the $1\alpha,3\beta,24$-trihydroxy-cholesta-4,6-diene. Furthermore it was found that there was hardly any difference in composition among these fractions, and the molar ratio of the 5,7-diene to the 4,6-diene remained at about 3:1. (See Comparative Example 3 below).

COMPARATIVE EXAMPLE 2

This Example illustrates the separation of $1\alpha,3\beta,24$-triacetoxy-cholesta-5,7-diene and $1\alpha,3\beta,24$-triacetoxy-cholesta-4,6-diene using a carrier containing silicon dioxide but not containing non-metallic silver (comparison with respect to the third step).

A mixture of $1\alpha,3\beta,24$-triacetoxy-cholesta-5,7-diene and $1\alpha,3\beta,24$-triacetoxy-cholesta-4,6-diene in a molar ratio of 3:1, which had been prepared in the same way as in Example 14, (A), and identified in the same way as in Example 14, (C), was subjected to preparative thin-layer chromatography using the same plate as used in Example 14, (D-1) and a silica gel carrier treated with silver nitrate (developing solvent, 0.4% methanol-chloroform). Only one spot was detected by UV spectrum at Rf = about 0.4.

This fraction was isolated to obtain an oily substance whose UV spectrum showed an absorption at 233, 240, 248, 262, 271, 282, and 294 nm.

Thus, it was found that the separation of $1\alpha,3\beta,24$-triacetoxycholesta-5,7-diene from $1\alpha,3\beta,24$-triacetoxy-cholesta-4,6-diene failed even when silica gel containing non-metallic silver was used as a carrier (see Comparative Example 4).

EXAMPLE 15

Separation of $1\alpha,3\beta,24(R)$-trihydroxy-cholesta-5,7-diene and $1\alpha,3\beta,24(R)$-trihydroxycholesta-4,6-diene (Third Step)

$1\alpha$-Hydroxy-$3\beta,24(R)$-dibenzoyloxy-cholest-5-ene prepared and separated in the same way as in Example 4, (B) was treated in the same way as in Example 5, (A) to form $1\alpha$-acetoxy-$3\beta,24(R)$dibenzoyloxy-cholest-5-ene. This product was treated in the same way as in Example 10 to afford a crude reaction mixture containing 1α-acetoxy-3β,24(R)-dibenzoyloxy-cholesta-5,7-diene. The crude mixture was hydrolyzed in the same way as in Example 14, (B), and separated by preparative thin-layer chromatography in the same way as in (D-1).

As a result, the reaction mixture containing 1α,3β,24(R)-trihydroxy-cholesta-5,7-diene and 1α,3β,24(R)-trihydroxy-cholesta-4,6-diene in a molar ratio of about 3:1 was distinctly separated into these two constituents.

The product separated from the spot based on 1α,3β,24(R)-trihydroxy-cholesta-5,7-diene had the following characteristics.

UV spectrum, $\lambda_{max}^{ethanol}$ (nm):
 262, 271 ($\epsilon$ = 11,000), 282 (11,800), 294 (7,000).
NMR spectrum ($C_3D_6O$):
 3.25 (1H, m, C-24-H),
 3.68 (1H, m, 1β-H),
 4.10 (1H, m, 3α-H),
 5.30 (1H, d, J = 6Hz, 6 or 7-H),
 5.60 (1H, d, J = 6Hz, 6 or 7-H),
Mass spectrum:
 416 (M$^+$), 398, 380, 357, 251, 227, 197, 157
Melting point (°C.):
 96°–99° C.

EXAMPLE 16

Separation of 1α,3β,24(S)-trihydroxy-cholesta-5,7-diene and 1α,3β,24(S)-trihydroxy-cholesta-4,6-diene (Third Step)

1α-Hydroxy-3β,24(S)-dibenzoyloxy-cholest-5-ene prepared and separated in the same way as in Example 4, (B) was treated in the same way as in Example 5, (A) to afford 1α-acetoxy-3β,24(S)-dibenzoyloxy-cholest-5-ene. This product was treated in the same way as in Example 10 to afford a crude reaction mixture containing 1α-acetoxy-3β,24(S)-dibenzoyl-cholesta-5,7-diene. This reaction mixture was hydrolyzed in the same way as in Example 14, (B), and separated by preparative thin-layer chromatography in the same way as in (D-1) above.

As a result, the above crude reaction mixture containing 1α,3β,24(S)-trihydroxy-cholesta-5,7-diene and 1α,3β,24(S)-trihydroxy-cholesta-4,6-diene in a molar ratio of about 3:1 could be separated distinctly into these constituents.

The product separated from the spot based on 1α,3β,24(S)-trihydroxy-cholesta-5,7-diene had the following characteristics.

UV spectrum, $\lambda_{max}^{ethanol}$ (nm):
 262, 271 (10,800), 282 (11,500), 294 (6,900)
NMR spectrum (in $C_3D_6O$):
 3.27 (1H, m, C-24-H),
 3.67 (1H, m, 1β-H),
 4.10 (1H, m, 3α-H),
 5.30 (1H, d, J = 6 Hz, 6 or 7-H),
 5.60 (1H, d, J = 6 Hz, 6 or 7-H)
Mass spectrum:
 416 (M$^+$), 398, 380, 357, 251, 227, 197, 157
Melting point (°C):
 120° to 124° C.

EXAMPLE 17

Synthesis of 1α,24-dihydroxycholecalciferol (Fourth Step)

16 mg of 1α,3β,24-trihydroxy-cholesta-5,7-diene prepared and separated in the same way as in Example 14, (D-1) was dissolved in 500 ml. of diethyl ether, and this solution was irradiated with ultraviolet rays for 2.5 minutes at 5° C. in an atmosphere of argon using a 200 W high pressure mercury lamp (654A-36, trademark for a product of Hanovia Company). A part of the solution was taken out, and its UV spectrum was determined. There was an increase in absorption at 262 to 263 nm which was considered to be due to 1α,24-dihydroxy-pre-cholecalciferol. After the reaction, ether was evaporated off at room temperature under reduced pressure. Benzene (50 ml.) was added to the residue, and isomerization was carried out for 2 hours under reflux of benzene.

After the reaction, the benzene was evaporated off at reduced pressure to afford 16 mg. of a white solid. This product was carefully separated by preparative thin-layer chromatography using a silica gel carrier containing about 1.5% of silver nitrate (obtained in the same way as in Example 14, (D-1) (developed twice with 6% methanol-chloroform). It showed three bands that could be confirmed by ultraviolet rays. From the least polar band, 2.8 mg of a white solid was obtained. This product had the following properties, and was identified as 1α,24-dihydroxycholecalciferol.

Figure 5:
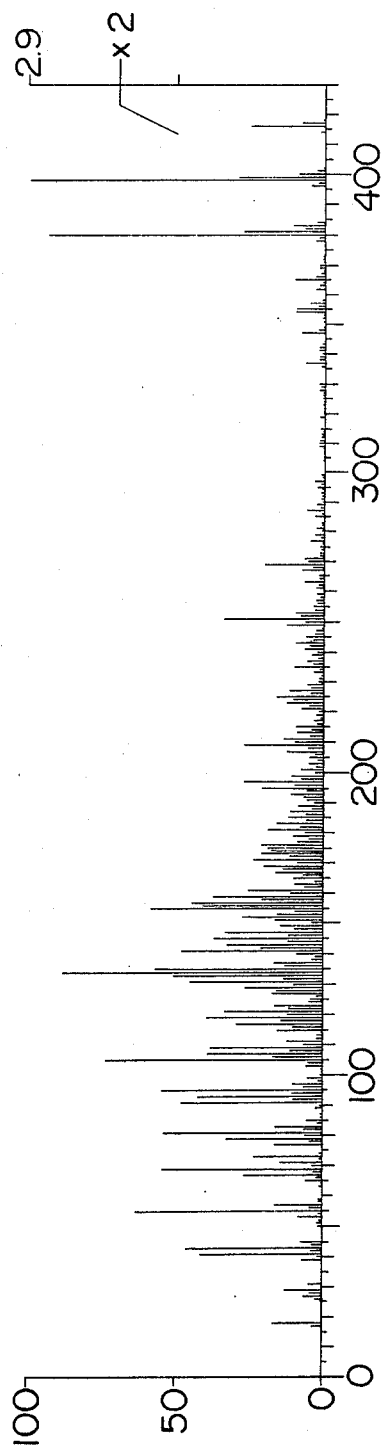

UV spectrum (FIG. 4):
 $\lambda_{max}^{ethanol}$ (nm) = 265
 $\lambda_{min}^{ethanol}$ (nm) = 228
NMR spectrum ($C_3D_6O$):
 0.57 (6H, d, 18-CH$_3$),
 0.87 (6H, d, J=7Hz, 26- & 27-CH$_3$),
 0.96 (3H, d, J=5Hz, 21-CH$_3$),
 3.19 (1H, m, 24-H),
 4.15 (1H, m, 1β-H),
 4.36 (1H, m, 3α-H),
 4.85 (1H, b, s, 19-H),
 5.30 (1H, b, s, 19-H),
 6.05 (1H, d, J$_{AB}$ = 11Hz, 6 or 7-H),
 6.26 (1H, d, J$_{AB}$ = 11Hz, 6 or 7-H),
Mass spectrum (FIG. 5):
 416 (M$^+$), 398, 380, 269, 251, 134,
High resolution mass spectrum:
 Found = 416.32768
 Require, M$^+$ ($C_{27}H_{44}O_3$) = 416.32927
Melting point (°C.):
 84° to 85° C.

EXAMPLE 18

Synthesis of 1α,24(R)-dihydroxycholecalciferol (Fourth Step)

10 mg of 1α,3β,24(R)-trihydroxyholesta-5,7-diene prepared and separated in the same way as in Example 15 was dissolved in 140 ml. of diethyl ether, and the resulting solution was irradiated with ultraviolet rays at 5° C. for 2 minutes. A part of the solution was taken out, and its UV spectrum was determined. An increase in absorption at 262 to 263 nm considered to be due to the precursor was observed. After the reaction, the ether was evaporated off at room temperature under reduced pressure. Benzene (50 ml.) was added to the residue, and isomerization was carried out for 2 hours in an atmosphere of argon under reflux of benzene.

After the reaction, the reaction mixture was treated in the same way as in Example 17, and separated and purified by preparative thin-layer chromatography. From the least polar band, 1.8 mg of a white solid was obtained. This product had the following properties, and was identified as 1α,24(R)-dihydroxy-cholecalciferol.

UV spectrum:
$\lambda_{max}^{ethanol}$ (nm) = 265
$\lambda_{min}^{ethanol}$ (nm) = 228

NMR spectrum ($C_3D_6O$):
0.59 (3H, s, 18-$CH_3$),
0.87 (6H, d, J=7Hz, 26-& 27-$CH_3$)
3.20 (1H, m, 29-H),
4.14 (1H, m, 1β-H),
4.42 (1H, m, 3α-H),
4.87 (1H, b, s, 19-H),
5.32 (1H, b, s, 19-H),
6.08 (1H, d, $J_{AB}$ = 11Hz, 6- or 7-H),
6.30 (1H, d, $J_{AB}$ = 11Hz, 6- or 7-H), Mass spectrum:
416 ($M^+$), 398, 380, 269, 251, High resolution mass spectrum:
Found = 416.33084
Require ($M^+$) = 416.32927 ($C_{27}H_{44}O_3$)

EXAMPLE 19

Synthesis of 1α,24(S)-dihydroxycholecalciferol (Fourth Step)

15 mg of 1α,3β,24(S)-trihydroxy-cholesta-5,7-diene prepared and separated in the same way as in Example 16 was dissolved in 140 ml. of diethyl ether, and the resulting solution was irradiated with ultraviolet rays for 2 minutes at 5° C. Then, the same procedure as in Example 18 was repeated to afford 2.8 mg of a white solid. This product had the following properties, and was identified as 1α,24(S)-dihydroxycholecalciferol.

UV sepctrum:
$\lambda_{max}^{ethanol}$ (nm)=265
$\lambda_{min}^{ethanol}$ (nm)=228

NMR spectrum (in $C_3D_6O$):
0.58 (3H, s, 18-$CH_3$),
0.87 (6H, d, J=7Hz, 26- and 27-$CH_3$),
3.20 (1H, m, 24-H),
4.14 (1H, m, 1β-H),
4.42 (1H, m, 3α-H),
4.87 (1H, b, s, 19-H),
5.32 (1H, b, s, 19-H),
6.08 (1H, d, $J_{AB}$=11Hz, 6- or 7-H),
6.30 (1H, d, $J_{AB}$=11Hz, 6- or 7-H), Mass spectrum:
416 ($M^+$), 398, 380, 269, 251, 134, High resolution mass spectrum:
Found = 416.33095
Require ($M^+$) = 416.32917 ($C_{27}H_{44}O_3$)

EXAMPLE 20

A. Synthesis of 1α,3β,24-triacetoxycholest-5,7-diene from 1α,3β,24-trihydroxycholesta-5,7-diene 200 mg of 1α,3β,24trihydroxycholesta-5,7-diene prepared and separated in the same way as in Example 14, (D-1) was reacted with 2ml. of acetic anhydride and 5 ml. of pyridine at 95° C. for 3 hours. The reaction mixture was placed in ice water, and extracted with 40 ml. of diethyl ether. The ethereal phase was washed with dilute hydrochloric acid, then with alkali, and further with water, and dried. The ether was evaporated off to afford 1α,3β,24-triacetoxycholesta-5,7-diene as a slightly yellowish oily substance.

B. Synthesis of 1α,24-diacetoxycholecalciferol-3β-acetate (Fourth Step)

50 mg of 1α,24-diacetoxycholecalciferol-3β-acetate was dissolved in 500 ml. of diethyl ether. The resulting solution was irradiated with ultraviolet rays in an atmosphere of argon at 5° C. for 4 minutes.

A part of this solution was taken out, and its UV spectrum was determined. An increase in absorption at 262 to 263 nm considered to be due to the precursor was observed. After the reaction, the ether was evaporated off at reduced pressure and at room temperature. Benzene (100 ml.) was added to the residue, and isomerization was carried out for 2 hours in an atmosphere of argon under reflux of benzene. After the reaction, most of the benzene was evaporated off at reduced pressure, and to the residue were added 2 ml. of 5% potassium hydroxide/methanol, 2 ml. of methanol and 2 ml. of benzene. The mixture was allowed to stand for one day at room temperature to perform hydrolysis. The reaction product was diluted with water, and extracted with ethyl acetate. The ethyl acetate phase was repeatedly washed with water, and dried. The ethyl acetate was then evaporated off at reduced pressure to afford 35 mg of a light yellow oily substance.

This substance was separated and purified by preparative thin-layer chromatography using a silica gel carrier containing silver nitrate in the same way as in Example 17. From the least polar band, 5.7 mg of a solid was obtained. Since the various spectra and properties of this product corresponded completely with those of the 1α,24-dihydroxycholecalciferol obtained in Example 17, the product obtained after isomerization was identified as 1α,24-diacetoxycholecalciferol-3-acetate.

EXAMPLE 21

A. Synthesis of 1α,3β,24-tribenzoyloxycholesta-5,7-diene from 1α,3β,24-trihydroxycholesta-5,7-diene 160 mg of 1α,3β,24-trihydroxycholesta-5,7-diene prepared and separated in the same way as in Example 14, (D-1) was reacted with 410 mg of benzoyl chloride and 15 ml. of pyridine.

The reaction mixture was diluted with water, and extracted with 40 ml. of diethyl ether. The ethereal phase was washed with dilute hydrochloric acid, then with alkali, and finally with water, and dried. The ether was evaporated off to afford 1α,3β,24-tribenzoyloxycholesta-5,7-diene as white amorphous product.

B. Synthesis of 1α,24-dibenzoyloxycholecalciferol-3β-benzoate (Fourth Step)

30 mg of 1α,3β,24-tribenzoyloxycholesta-5,7-diene was dissolved in 500 ml. of benzene, and the resulting solution was irradiated with ultraviolet rays in an atmosphere of argon at 10° C. for 2 minutes. After the reaction, isomerization was carried out for 2 hours in the argon atmosphere under reflux of benzene. After the reaction, most of the benzene was evaporated off at reduced pressure, and 2 ml. of 5% potassium hydroxide-methanol and 2 ml. of benzene were added to the residue. The mixture was maintained at room temperature for 28 hours in an atmosphere of argon to perform hydrolysis. The reaction product was diluted with water, and extracted with ethyl acetate. The ethyl acetate layer was repeatedly washed with water, and dried. The ethyl acetate was evaporated off at reduced pressure. The residue was subjected to the same separating and purifying procedure as in Example 20 to afford 1.9 mg of 1α,24-dihydroxycholecalciferol having the same properties as the product obtained in Example 20.

From this result, the product obtained after the isomerization reaction was identified as 1α,24-dibenzoylcholecalciferol-3-benzoate.

EXAMPLE 22

A. Synthesis of 1α-hydroxy-3β,24-dibenzoyloxycholesta-5,7-diene from 1α,3β,24-trihydroxycholesta-5,7-diene 250 mg of 1α,3β,24-trihydroxycholesta-5,7-diene prepared in the same way as in Example 14, (D-1) was mixed with 210 mg of benzoyl chloride and 5 ml. of pyridine, and the mixture was allowed to stand at 23° C. for one day. The resulting reaction mixture was treated in the same way as in Example 21 to afford 1α-hydroxy-3β,24-dibenzoyloxycholesta-5,7-diene.

B. Synthesis of 1α-hydroxy-24-benzoyloxycholecalciferol-3β-benzoate (Fourth Step)

20 mg of 1α-hydroxy-3β,24-dibenzoyloxycholesta-5,7-diene was dissolved in 500 ml. of diethyl ether. The solution was irradiated with ultraviolet rays, isomerized, and hydrolyzed in the same way as in Example 21, (B) to afford 1.9 mg of 1α,24-dihydroxycholecalciferol which showed the same properties as the product obtained in Example 20.

From this result, it was confirmed that the product obtained after the above isomerization reaction was 1α-hydroxy-24-benzoylcholecalciferol-3β-benzoate.

EXAMPLE 23

Synthesis of 1α,24(R)-diacetoxycholecalciferol-3β-acetate (Fourth Step)

The 1α,3β,24(R)-trihydroxycholesta-5,7-diene obtained in Example 15 was acetylated in the same way as in Example 20, (A) to obtain 1α,3β,24(R)-trihydroxycholesta-5,7-diene. 25 mg of this product was treated in the same way as in Example 20, (B) except that the irradiation of ultraviolet rays was performed for 2 minutes. There was obtained 3.4 mg of a product whose properties correspond with those of 1α,24(R)-dihydroxycholecalciferol.

From this result, it was confirmed that the product obtained after the isomerization reaction was 1α,24(R)-diacetoxycholecalciferol-3β-acetate.

EXAMPLE 24

Synthesis of 1α,24(R)-dibenzoyloxycholecalciferol-3β-benzoate (Fourth Step)

The 1α,3β,24(R)-trihydroxycholesta-5,7-diene was benzoylated in the same way as in Example 21, (A) to obtain 1α,3β,24(R)-tribenzoyloxycholesta-5,7-diene. This product was treated in the same way as in Example 21, (B) except that 30 mg of this product was used, and the irradiation of ultraviolet rays was performed at 12° C. for 2 minutes. There was obtained 3.4 mg of a product whose properties corresponded with those of 1α,24(R)-dihydroxycholecalciferol.

From this, the product after the isomerization reaction was identified as 1α,24(R)-dibenzoyloxy-cholecalciferol-3β-benzoate.

EXAMPLE 25

Synthesis of 1α-hydroxy-24(R)-benzoyloxy-cholecalciferol-3β-benzoate (Fourth Step)

The 1α,3β,24(R)-trihydroxy-cholesta-5,7-diene was benzoylated in quite the same way as in Example 22, (A) to form 1α-hydroxy-3β,24(R)-dibenzoyloxy-cholesta-5,7-diene.

10 mg of this product was treated in the same way as in Example 22, (B) to afford 1.2 mg of a product whose properties corresponded with those of the 1α,24(R)-dihydroxycholecalciferol.

From this result, it was confirmed that the product after the isomerization was 1α-hydroxy-24(R)-benzoyloxy-cholecalciferol-3β-benzoate.

EXAMPLE 26

Synthesis of 1α,24(S)-diacetoxy-cholecalciferol-3β-acetate (Fourth Step)

The 1α,3β,24(S)-trihydroxycholesta-5,7-diene obtained in Example 16 was acetylated in the same way as in Example 20, (A) to form 1α,3β,24(S)-trihydroxy-cholesta-5,7-diene. 20 mg of this product was treated in the same way as in Example 23 to afford 3.1 mg of a product whose properties corresponded with those of the 1α,24(S)-dihydroxycholecalciferol.

From this result, it was confirmed that the product after the isomerization reaction was 1α,24(S)-diacetoxycholecalciferol-3β-acetate.

EXAMPLE 27

Synthesis of 1α-hydroxy-24(S)-benzoyloxy-cholecalciferol-3β-benzoate (Fourth Step)

The 1α,3β,24(S)-trihydroxycholesta-5,7-diene obtained in Example 16 was benzoylated in quite the same way as in Example 22, (A) to form 1α-hydroxy-3β,24(S)-dibenzoyloxycholesta-5,7-diene. 15 mg of this product was treated in quite the same way as in Example 25 to afford 1.5 mg of a product whose properties corresponded with 1α,24(S)-dihydroxycholecalciferol. From this, it was confirmed that the product obtained after the isomerization was 1α-hydroxy-24(S)-benzoyloxycholecalciferol-3β-benzoate.

EXAMPLE 28

Synthesis of 1α-acetoxy-24(S)-benzoyloxy-cholecalciferol-3β-benzoate (Fourth Step)

1α-Hydroxy-3β,24(S)-dibenzoyloxycholesta-5,7-diene obtained in the same way as in Example 27 was acetylated in the same way as in Example 26 to form 1α-acetoxy-3β,24(S)-dibenzoyloxycholesta-5,7-diene.

15 mg of this product was treated in the same way as in Example 26 except that the irradiation of ultraviolet rays was carried out at 8° C. for 1 minute. There was obtained 1.5 mg of a product whose properties corresponded with those of 1α,24(S)-dihydroxy-cholecalciferol. From this, it was confirmed that the product obtained after the isomerization was 1α-acetoxy-24(S)-benzoyloxy-cholecalciferol-3β-benzoate.

COMPARATIVE EXAMPLE 3

Synthesis of 1α,24-dihydroxy-cholecalciferol from 1α,3β,24-trihydroxycholesta-5,7-diene contaiming 1α,3β,24-trihydroxycholesta-4,6-diene (Comparison With Respect to the Fourth Step)

10 mg of a mixture of 1α,3β,24-trihydroxy-cholesta-5,7-diene and 1α,3β,24-trihydroxy-cholestra-4,6-diene in a molar ratio of about 3:1 obtained in the same way as in Comparative Example 1 was dissolved in 500 ml. of diethyl ether, and the solutionn was irradiated with ultraviolet rays at 5° C. for 2 minutes. After the reaction, the diethyl ether was carefully evaporated off at reduced pressure. To the residue was added 50 ml. of benzene, and isomerization was carried out in an atmosphere of argon for 2 hours under reflux of benzene. After the reaction, the benzene was evaporated off to afford 10 mg of a brown oil substance.

The UV spectrum of this product was complicated. In particular, it was devoid of a specific absorption of 1α,24-dihydroxy-cholecalciferol which exhibits an absorption maximum at 265 nm, and the formation of 1α,24-dihydroxy-cholecalciferol could not be confirmed.

This was confirmed by subjecting the above substance to preparative thin-layer chromatography using a silica gel carrier having absorbed thereto silver nitrate, and comparing the chromatogram with that of a standard sample of 1α,24-dihydroxycholecalciferol. The product did not show any spot which corresponded to the standard sample.

It can be seen therefore that when the purity of 1α,3β,24-trihydroxy-cholesta-5,7-diene is low, 1α,3β,24-trihydroxycholecalciferol is not formed at all by isomerization using ultraviolet irradiation.

COMPARATIVE EXAMPLE 4

Synthesis of 1α,24-diacetoxy-cholecalciferol-3β-acetate from 1α,3β,24-triacetoxycholesta-5,7-diene containing 1α,3β,24-triacetoxycholesta-4,6-diene (comparison of fourth step)

10 mg of a mixture consisting of 1α,3β,24-triacetoxy-cholesta-5,7-diene and 1α,3β,24-triacetoxy-4,6-diene in a molar ratio of about 3:1 obtained in the same way as in Comparative Example 2 was dissolved in 500 ml. of diethyl ether, and the solution was irradiated with ultraviolet rays at 5° C. for 2 minutes. The reaction mixture turned yellowish brown. After the reaction, the diethyl ether was carefully evaporated off at reduced pressure. Benzene (50 ml.) was added to the residue, and isomerization was carried out for 2 hours in an atmosphere of argon under reflux of benzene. After the reaction, most of the benzene was evaporated off at reduced pressure. To the residue was added 1 ml. of 5% potassium hydroxide-methanol, and the mixture was allowed to stand at room temperature for 24 hours in an atmosphere of argon to perform hydrolysis. After the reaction, the benzene was evaporated off, and its UV spectrum was determined. The product was subjected to preparative thin-layer chromatography. The results were quite the same as in Comparative Example 3, and no formation of 1α,24-dihydroxycholecalciferol was observed.

EXAMPLE 29

Effect of promoting intestinal calcium transport by 1α,24-dihydroxycholecalciferol (1α,24-DHCC)

a. Comparison with 1α-hydroxycholecalciferol (1α-HCC)

Male Wistar rats with a body weight of about 200 g were fasted overnight, and then orally administered with 625 p moles of a solution of each of 1α,24-DHCC and 1α-HCC in corn oil. After a predetermined period of time, a solution of radioactive calcium chloride ($^{45}$Ca Cl$_2$, 30 μCi/ml) was administered orally. The radioactivity level in blood was measured over the course of 10 to 60 minutes. The maximum value was made an index of intestinal calcium absorption.

A control group of rats was administered with corn oil alone in the same amount. The dosages of the corn oil solution of 1α,24-DHCC or 1α-HCC and the corn oil were 0.0125 ml per 100 g of the body weight of each rat, and the dosage of the radioactive calcium chloride aqueous solution (pH 7.0) was 0.1 ml per 100 g of the body weight of each rat.

The radioactivity level was measured by placing 0.2 ml. of serum in a Vial bottle, adding 12 ml. of a cocktail containing a scintillator (containing 1200 ml of toluene, 800 ml of ethyl cellosolve, 8 g of 2,5-diphenyloxazole, and 300 mg of 2,2'-p-phenylenebis(5-phenyloxazole)), and determining the radioactivity by means of a liquid scintillation counter. The results are shown in Table 1.

Table 1

| Time after administration (hours) | Radioactivity in serum (cpm) | | | |
|---|---|---|---|---|
| | 1α,24-DHCC | | 1α-HCC | |
| Control | 275 ± 95 | (4)* | 275 ± 95 | (4) |
| 4 | 360 ± 150 | (4) | 697 ± 221 | (4) |
| 8 | 996 ± 80 | (4) | 1035 ± 150 | (4) |
| 12 | 924 ± 130 | (4) | 643 ± 210 | (4) |
| 24 | 426 ± 61 | (4) | 332 ± 28 | (4) |

*The numbers in the parentheses show the number of rats in a particular group.

The above results demonstrate that 1α,24-DHCC has nearly an equivalent effect to 1α-HCC with regard to the promotion of intestinal calcium absorption.

b. Comparison between 1α,24(R)-DHCC and 1α,24(S)-DHCC

Male Wistar rats were fasted overnight, and then orally administered with 625 p moles of a solution of each of 1α,24(R)-DHCC and 1α,24(S)-DHCC in corn oil. Eight hours after the administration, the rats were killed, and intestinal calcium absorption was determined by the everted gut sac method [Martin, D. L. and H. F. DeLuca, Amer. J. Physiol. 216, 1351 (1969)]. The results are shown in Table 2.

Table 2

| | $^{45}$Ca (S/M) |
|---|---|
| Control | 1.29 ± 0.16 (4)* |
| 1α,24(R)-DHCC | 5.86 ± 1.98 (4) |
| 1α,24(S)-DHCC | 2.68 ± 0.80 (4) |

The numbers in the parentheses show the number of rats in a particular group.

The experimental conditions were as follows:
Intestinal tract used: duodenum, 7 cm
Amount of the medium poured in the everted duodenum: 0.7 ml

Composition of the medium:

| | |
|---|---|
| NaCl | 125 mM |
| Fructose | 10 mM |
| Tris-Cl buffer | 30 mM (pH 7.4) |
| $CaCl_2$ | 0.25 mM |
| $45_{CaCl_2}$ | 10 μCi/l |

Incubation conditions:
37° C., 90 minutes
a gaseous mixture of 95% $O_2$
and 5% $CO_2$ was passed
Amount of the liquid used for radioactivity measurement: 0.1 ml
Other conditions were the same as in (a) above.

The above results demonstrate that 1α,24(R)-DHCC exhibited a greater effect of promoting intestinal calcium absorption than 1α,24(S)-DHCC.

EXAMPLE 30

Comparison of 1α-HCC, 1α,24-DHCC, 1α,24(R)-DHCC and 1α,24(S)-DHCC with Regard to the Effect of Promoting Intestinal Calcium Absorption The experimental procedure was quite the same as in Example 29, (b). The results obtained are shown in Table 3.

Table 3

| Dose | 125 p mole | 625 p mole | 3,125 p mole |
|---|---|---|---|
| Control | | 3.31 ± 0.12 (15)* | |
| 1α-HCC | 3.59 ± 0.23 (4) | 4.10 ± 0.27 (4) | 5.10 ± 0.27 (4) |
| 1α,24-DHCC | 4.12 ± 0.25 (4) | 4.84 ± 0.32 (4) | 5.47 ± 0.33 (4) |
| 1α,24(S)-DHCC | 3.97 ± 0.28 (4) | 4.17 ± 0.31 (4) | 5.18 ± 0.20 (4) |
| 1α,24(R)-DHCC | 4.42 ± 0.41 (4) | 5.93 ± 0.33 (4) | 5.84 ± 0.39 (4) |

The numbers in the parentheses show the number of rats in a particular group.

The results shown in Table 3 led to the reconfirmation of the experimental results in Example 29. In order words, with regard to intestinal calcium absorption, 1α,24-DHCC has at least an equivalent activity to 1α-HCC, and among 1α,24-DHCC, 1α,24(R)-DHCC and 1α,24(S)-DHCC, the following relation holds good with regard to the degree of activity of promoting intestinal calcium absorption.

1α,24(R)-DHCC > 1α,24-DHCC > 1α,24(S)-DHCC

EXAMPLE 31

Comparison of Bone Absorption Effect Between 1α,24-DHCC and 1α-HCC

Male wistar rats (each with a body weight of about 150 g) were subcutaneously administered with an aqueous solution of $^{45}CaCl_2$ in a dose of 50 μCi per rat, and kept for 6 weeks. $^{45}Ca$ so administered was rapidly absorbed, and a greater portion of it gathered at the bones in several hours. Three weeks later, the $^{45}Ca$ level in blood became constant, and only the bones were in the specifically labelled state. This was confirmed by a macroautoradiographic analysis of the whole body. After keeping the rats for 6 weeks, they were orally administered continuously once a day with a solution of 2,125 P moles each of 1α-HCC and 1α,24-DHCC. Blood was taken out with the passage of time, and the serum radioactivity level was measured by the method described in Example 29 (a). An increase in the serum radioactivity level was made an index of the effect of bone absorption. The control group was administered with corn oil alone. The number of rats tested was 4 in each group. The results obtained are shown in FIG. 6. In this figure, the symbol * indicates a significant difference in serum radioactivity level from the control.

As can be seen from the results shown in FIG. 6, with 1α-HCC, bone absorption increased significantly two days after the start of administration, and this tendency became greater with time. On the other hand, with 1α,24-DHCC, bone absorption increased significantly only after a lapse of 4 days, but after that, the degree of increase was far lower than with 1α-HCC (about ⅓ on the eight day). This appears to suggest that 1α,24-DHCC exhibits a weaker bone absorbing effect than 1α-HCC, and is lower in toxicity.

EXAMPLE 32

Comparison of Bone Absorbing Effect and Body Weight Change Among 1α-HCC, 1α,24-DHCC, 1α,24(R)-DHCC, and 1α,24(S)-DHCC A similar test to Example 31 was performed on the above four compounds. Unlike Example 31, the experiment was begun three weeks after the administration of $^{45}CaCl_2$. Both the serum radioactivity level and the total calcium concentration in the serum were measured. For the measurement of the calcium concentration, a calcium measuring kit (made by Iatron Company) was used. The results obtained are shown in Tables 4 and 5.

Table 4

| | Serum $^{45}Ca$ level | | | |
|---|---|---|---|---|
| Time | Serum radiactivity (cpm) | | | |
| (days) | 0 | 5 | 7 | 9 |
| Control | 699 ± 53.7 | 621 ± 48.6 | 597 ± 33.9 | 600 ± 49.3 |
| 1α-HCC | 690 ± 39.4 | 1056 ± 66.8 | 1184 ± 51.1 | 904 ± 57.1 |
| 1α,24-DHCC | 675 ± 54.9 | 948 ± 64.6 | 700 ± 32.8 | 661 ± 78.8 |
| 1α,24(R)-DHCC | 648 ± 44.3 | 874 ± 30.4 | 778 ± 26.9 | 681 ± 63.7 |
| 1α,24(S)-DHCC | 780 ± 43.5 | 539 ± 45.2 | 520 ± 53.8 | 609 ± 91.5 |

Table 5

| Time (days) | Serum Ca level Serum Ca (mg/dl) | | | |
| --- | --- | --- | --- | --- |
| | 0 | 5 | 7 | 9 |
| Control | 11.4 ± 0.32 | 10.0 ± 0.29 | 11.1 ± 0.22 | 10.6 ± 0.15 |
| 1α-HCC | 10.4 ± 0.21 | 14.1 ± 0.29 | 14.7 ± 0.33 | 13.8 ± 0.41 |
| 1α,24-DHCC | 11.7 ± 0.26 | 12.9 ± 0.18 | 11.5 ± 0.23 | 12.1 ± 0.19 |
| 1α,24(R)-DHCC | 11.3 ± 0.35 | 12.6 ± 0.23 | 13.3 ± 0.25 | 12.8 ± 0.35 |
| 1α,24(S)-DHCC | 11.2 ± 0.16 | 11.5 ± 0.33 | 11.2 ± 0.29 | 11.5 ± 0.24 |

From the results shown in Tables 4 and 5, the experimental results in Example 31 were re-confirmed. In other words, these results show that 1α,24-DHCC is far weaker in bone absorbing effect than 1α-HCC, and among 1α,24-DHCC, 1α,24(R)-DHCC and 1α,24(S)-DHCC, the following relation holds good with regard to the bone absorbing effect.

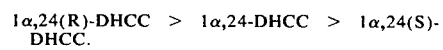

What is particularly noteworthy is that scarcely any bone absorbing effect is observed with 1α,24(S)-DHCC, and its effect is almost equivalent to the control. Accordingly, this indicates that 1α,24(S)-DHCC has an action of specifically promoting intestinal calcium absorption, and this is considered to be of utmost importance for clinical applications.

Changes in body weight was determined by the present experiment are shown in FIG. 7. It is interesting to note that 1α,24-DHCC causes a lesser degree of change in body weight than 1α,-HCC, and in particular, 1α,24(S)-DHCC shows little difference from the control group. This also suggest that similarly to the case of bone absorption, the toxicity of 1α,24-DHCC is lower than that of 1α-HCC.

EXAMPLE 33

COMPARISON OF TOXICITY BETWEEN 1α,24-DHCC AND 1α-HCC

The toxicity of each of the above two compounds was tested by a well known method. The results are shown in Table 6.

Table 6

| Species | Sex | Method of administration | ID$_{50}$ (μg/kg) | |
| --- | --- | --- | --- | --- |
| | | | 1α-HCC | 1α,24-DHCC |
| Mouse | ♂ | Peros | 474 | >2500 |
| | ♀ | | 508 | |
| | ♂ | Intravenous | 167 | 33,000 – 3,300 |
| | ♀ | | 100 | 3,300 – 1,000 |
| | ♂ | Peros | 330 | — |
| | ♀ | | 744 | — |

It is clear from the above table that the toxicity of 1α,24-DHCC is one-tenth or less of that of 1α-HCC. This result can also be suggested by the results of Examples 31 and 32.

On the basis of the results obtained in Examples 29 to 33, the characteristics of 1α,24-DHCC can be compared with those of 1α-HCC as shown in Table 7. In these data, the activity of 1α-HCC is set at 1.

Table 7

| | 1α,24-DHCC | 1α-HCC |
| --- | --- | --- |
| Effecto of promoting intestinal calcium | 1 | 1 |

Table 7-continued

| | 1α,24-DHCC | 1α-HCC |
| --- | --- | --- |
| absorption | | |
| Bone absorbing effect | less than 1/3 | 1 |
| Acute toxicity | less than 1/10 | 1 |

Since it has been demonstrated that 1α-24-DHCC in accordance with this invention selectively promotes intestinal calcium absorption and exhibits a weak bone absorbing effect as compared with the known analogs of active form of vitamin D$_3$, it is considered to be very useful as medicines that can be applied with little side-effects to the treatment of diseases induced by abnormal metabolism of calcium. In particular, 1α,24(S)-DHCC is a very desirable substance in this regard, and is expected to come into wide use.

What we claim is:

1. A mixture in arbitrary ratios of 1α,24(S)-dihydroxycholecalciferol and 1α,24(R)-dihydroxycholecalciferol expressed by the following formula

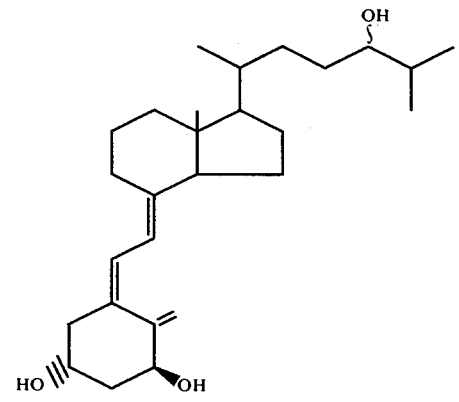

2. 1α,24(S)-dihydroxycholecalciferol expressed by the following formula

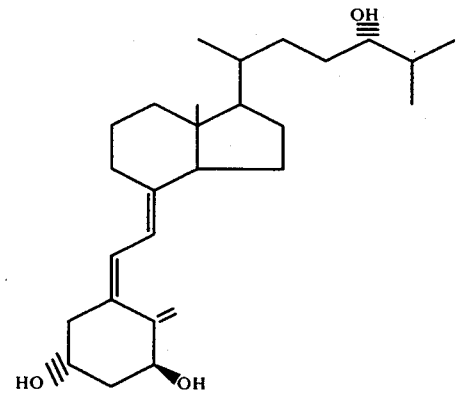

3. 1α,24(R)-dihydroxycholecalciferol expressed by the following formula

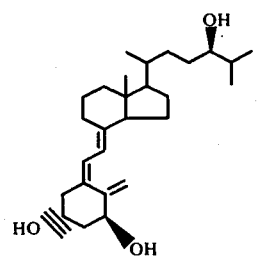

4. A 1α,24(S)-dihydroxycholecalciferol derivative, a 1α,24(R)-dihydroxycholecalciferol derivative, or a mixture of these in arbitrary ratios, expressed by the following formula

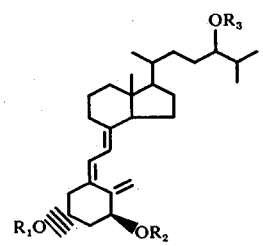

wherein $R_1$, $R_2$ and $R_3$ are identical or different and represent a hydrogen atom or a protective group convertible to a hydrogen atom which is selected from the group consisting of $C_1$–$C_{12}$ aliphatic and aromatic carboxylic acid residues and their nitrogen-, halogen-, and alkoxy-substituted derivatives, tert.-butyl, benzyl, triphenyl-methyl, tetrahydropyranyl, methoxy methyl and alkyl-substituted silyl with the proviso that at least one of $R_1$, $R_2$ and $R_3$ is said protective group.

5. A mixture in arbitrary ratios of 1α,3β,24(S)-trihydroxycholesta-5,7-diene or its derivative and 1α,3β,24(R)-trihydroxycholesta-5,7-diene or its derivative, expressed by the following formula

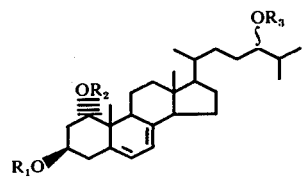

wherein $R_1$, $R_2$ and $R_3$ are identical or different and represent a hydrogen atom or a protective group convertible to a hydrogen atom which is selected from the group consisting of $C_1$–$C_{12}$ aliphatic and aromatic carboxylic acid residues and their nitrogen-, halogen-, and alkoxy-subsituted derivatives, tert.-butyl, benzyl, triphenyl-methyl, tetrahydropyranyl, methoxy methyl and alkyl-substituted silyl.

6. 1α,3β,24(S)-trihydroxycholesta-5,7-diene or a derivative thereof resulting from the protection of at least one hydroxyl group thereof, expressed by the following formula

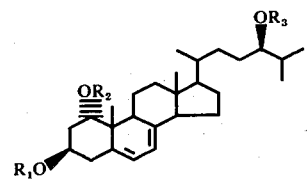

wherein $R_1$, $R_2$ and $R_3$ are identical or different and represent a hydrogen atom or a protective group convertible to a hydrogen atom which is selected from the group consisting of $C_1$–$C_{12}$ aliphatic and aromatic carboxylic acid residues and their nitrogen-, halogen-, and alkoxy-substituted derivative, tert.-butyl, benzyl, triphenyl-methyl, tetrahydropyranyl, methoxy methyl and alkyl-substituted silyl.

7. 1α,3β,24(R)-trihydroxycholesta-5,7-diene or a derivative thereof resulting from the protection of at least one hydroxyl group thereof, expressed by the following formula

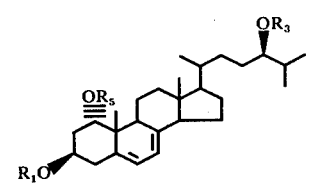

wherein $R_1$, $R_2$ and $R_3$ are identical or different and represent a hydrogen atom or a protective group convertible to a hydrogen atom which is selected from the group consisting of $C_1$–$C_{12}$ aliphatic and aromatic carboxylic acid residues and their nitrogen-, halogen-, and alkoxy-substituted derivatives, tert.-butyl, benzyl, triphenyl-methyl, tetrahydropyranyl, methoxy methyl and alkyl-substituted silyl.

8. 1α,24-dihydroxycholesterol or a derivative thereof resulting from the protection of at least one hydroxy group thereof, expressed by the following formula

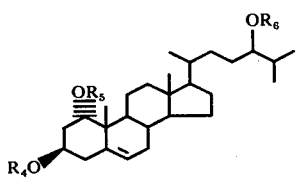

(2)

wherein $R_4$, $R_5$ and $R_6$ are identical or different and represent a hydrogen atom or a protective group convertible to a hydrogen atom which is selected from the group consisting of $C_1$–$C_{12}$ aliphatic and aromatic carboxylic acid residues and their nitrogen-, halogen-, and alkoxy-substitued derivatives, tert.-butyl, benzyl, triphenyl-methyl, tetrahydropyranyl, methoxy methyl and alkyl-substituted silyl.

9. 1α,24(S)-dihydroxycholesterol or a derivative thereof resulting from the protection of at least one hydroxyl group thereof, expressed by the following formula

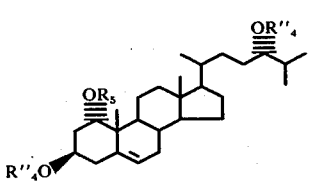

(2-c)

wherein $R''_4$ is a hydrogen atom or a substituted or unsubstituted benzoyl group, and $R_5$ is a hydrogen atom or a protective group convertible to a hydrogen atom which is selected from the group consisting of $C_1$–$C_{12}$ aliphatic and aromatic carboxylic acid residues and their nitrogen-, halogen-, and alkoxy-substituted derivatives, tert.-butyl, benzyl, triphenylmethyl, tetrahydropyranyl, methoxy methyl and alkyl-substituted silyl.

10. 1α,24(R)-dihydroxycholesterol or a derivative thereof resulting from the protection of at least one hydroxyl group thereof, expressed by the following formula

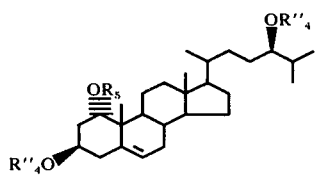

wherein R''₄ is a hydrogen atom or a substituted or unsubstituted benzoyl group and R₅ is a hydrogen atom or a protective group convertible to a hydrogen atom which is selected from the group consisting of C₁–C₁₂ aliphatic and aromatic carboxylic acid residues and their nitrogen-, halogen-, and alkoxy-substituted derivatives, tert.-butyl, benzyl, triphenylmethyl, tetrahydropyranyl, methoxy methyl and alkyl-substituted silyl.

11. 1α,2α-epoxy-24-ketocholesta-4,6-dien-3-one of the following formula

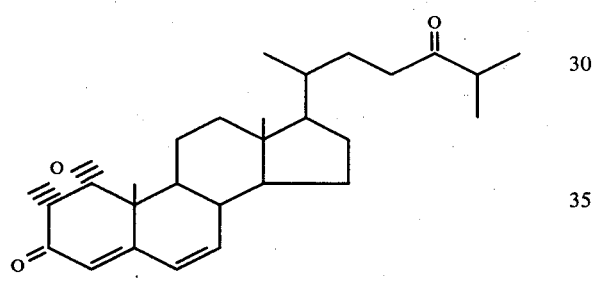

12. A process for preparing 1α,24-dihydroxycholesterol of the following formula

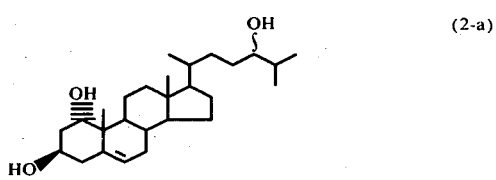

which comprises reacting 1α,2α-epoxy-24-keto-cholesta-4,6-dien-3-one of the formula

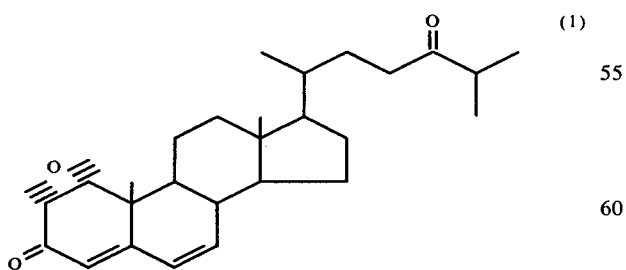

with an alkali metal and a proton donor in the presence of liquid ammonia or a liquid amine.

13. A process for recovering a benzoyl derivative of 1α,24(S)-dihydroxycholesterol and a benzoyl derivative of 1α,24(R)-dihydroxycholesterol, which comprises separating a benzoyl derivative of 1α,24-dihydroxycholesterol of the following formula

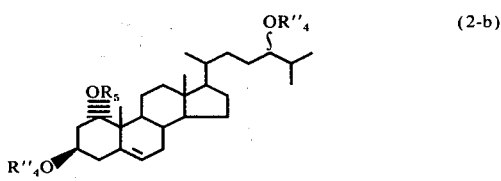

wherein R''₄ is a substituted or unsubstituted benzoyl group, and R₅ is a hydrogen atom or a protective group convertible to a hydrogen atom which is selected from the group consisting of C₁–C₁₂ aliphatic and aromatic carboxylic acid residues and their nitrogen-, halogen-, and alkoxy-substituted derivatives, tert.-butly, benzyl, triphenylmethyl, tetrahydropyranyl, methoxy methyl and alkyl-substituted silyl,
into a 1α,24(S)-epimer and a 1α,24(R)-epimer by chromatography using a carrier at least containing silicon dioxide.

14. A process for preparing at least one of a 1α,3β,24(S)-trihydroxycholesta-5,7-diene derivative and a 1α,3β,24(R)-trihydroxycholesta-5,7-diene derivative expressed by the following formula

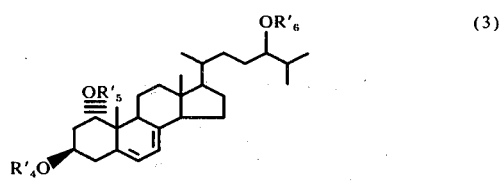

wherein R'₄, R'₅ and R'₆ are identical or different, and represent a protective group convertible to a hydrogen atom without changing the structure of formula (3) which is selected from the group consisting of C₁–C₁₂ aliphatic and aromatic carboxylic acid residues and their nitrogen-, halogen-, and alkoxy-substituted derivatives, tert.-butyl, benzyl, triphenylmethy, tetrahydropyranyl, methoxy methyl and alkyl-substituted silyl, which comprises reacting at least one of a 1α,24(S)-dihydroxycholesterol derivative and a 1α,24(R)-dihydroxycholesterol derivative expressed by the following formula

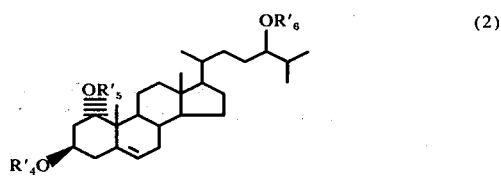

wherein R'₄, R'₅ and R'₆ are the same as defined above, with an allylic brominating agent selected from the group consisting of N-bromosuccinimide, 1,3-dibromo-5,5-dimethyl hydantoin and N-bromocaprolactam in an inert organic medium, and then contacting the resulting reaction mixture with a dehydrobrominating agent selected from the group consisting of trimethyl phosphite, S-collidine and diethylaniline.

15. A process for separating and recovering at least one of 1α,3β,24(S)- and 1α,3β,24(R)-trihydroxycholesta-5,7-diene from trihydroxycholesta-4,6-diene by a chromatographic procedure, which comprises contacting a mixture at least containing at least one of 1α,3β,24(S)- and 1α,3β,24(R)-trihydroxycholesta-5,7-diene of the followng formula

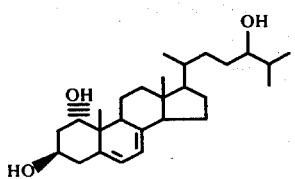
(3-a)

and trihydroxycholesta-4,6-diene of the following formula

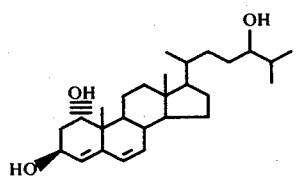
(4)

as a solution in an inert organic solvent with a carrier containing silicon dioxide and having adsorbed thereto non-metallic silver.

16. A process for preparing at least one of 1α,24(S)- and 1α,24(R)-dihydroxycholecalciferol of the followng formula

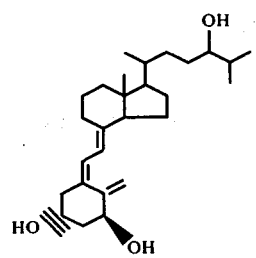
(5-a)

which comprises hydrolyzing or reductively decomposing at least one of protected 1α,24(S)- and 1α,24(R)-dihydroxycholecalciferol expressed by the following formula

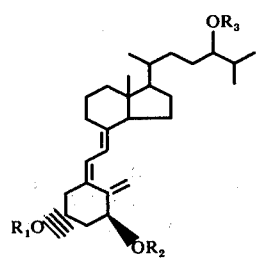
(5')

wherein $R_1$, $R_2$ and $R_3$ are the same or different and represent a hydrogen atom or a protective group convertible to hydrogen which is selected from the group consisting of $C_1$–$C_{12}$ aliphatic and aromatic carboxylic acid residues and their nitrogen-, halogen-, and alkoxy-substituted derivatives, tert.-butyl, benzyl, triphenylmethyl, tetrahydropyranyl, methoxy methyl and alkyl-substituted silyl, with the proviso that at least one of $R_1$, $R_2$ and $R_3$ represents a protective group convertible to a hydrogen atom, thereby to split off the protective group wherein when the protective group is the $C_1$–$C_{12}$ aliphatic or aromatic carboxylic acid residue or the nitrogen-, halogen- and alkoxy-substituted derivatives thereof, the protective group is split off by hydrolyzing with an alkali solution of an alcohol or by reductively decomposing with lithium-aluminum tetrahydride; and when the protective group is the tert.-butyl, benzyl, triphenylmethyl, tetrahydropyranyl, methoxy methyl or alkyl-substituted silyl group, the protective group is split off by hydrolyzing with an acid or alkali or by reductively decomposing with lithium-aluminum tetrahydride.

17. A pharmaceutically effective composition for warmblooded animals comprising a pharmaceutically effective amount of at least one of 1α,24(S)- and 1α,24(R)-dihydroxycholecalciferols of the formula

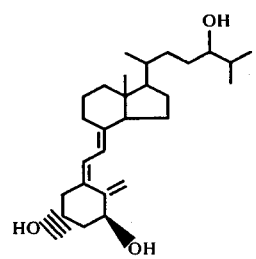
(5-a)

18. A pharmaceutical composition for warm-blooded animals according to claim 17 which is administrable orally or by intramuscular or intravenous injection, said composition comprising a pharmaceutically effective amount of at least one of the 1α,24(S)- and 1α,24(R)-dihydroxycholecalciferols of formula (5-a) and a vehicle non-toxic to warm-blooded animals.

19. A pharmaceutical composition for controlling calcium metabolism of warm-blooded animals according to claim 17 which comprises a pharmaceutically effective amount of at least one of the 1α,24(S)- and 1α,24(R)-dihydroxycholecalciferols of formula (5-a) and a vehicle non-toxic to warm-blooded animals.

20. A prophylactic or therapeutic pharmaceutical composition for vitamin D deficient diseases and related diseases according to claim 17, which comprises a pharmaceutically effective amount of at least one of the 1α,24(S)- and 1α,24(R)-dihydroxycholecalciferols of formula (5-a).

21. A method for controlling the calcium metabolism of warm-blooded animals, which comprises administering a pharmaceutically effective amount of at least one of the 1α,24(S)- and 1α,24(R)-dihydroxycholecalciferols of formula (5a)

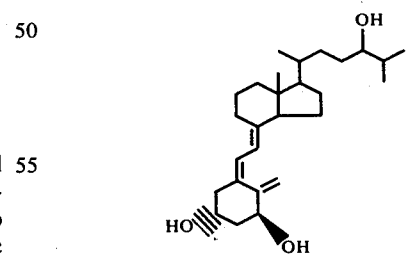
(5-a)

orally, subcutaneously, intramuscularly or intravenously.

22. The method of claim 21 wherein the effective amount is 0.01 to 10 μg daily per kilogram body weight of the warm-blooded animal.

23. A method for preventing or treting vitamin D deficiency-induced diseases or related diseases of man according to claim 21, which comprises administering to a human a pharmaceutically effective amount of at least one of the 1α,24(S)- and 1α,24(R)-dihydroxycholecalciferols of formula (5-a) orally, subcutaneously, intramuscularly or intravenously.

24. A method for treating vitamin D resistant hypocalcemia and bone diseases, which comprises administering at least one of the 1α,24(S)- and 1α,24(R)-dihydroxycholecalciferols of formula (5-a)

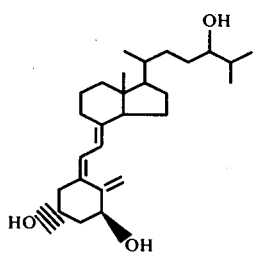
(5-a)

to a patient in a disage of 0.01 to 10 μg per kilogram of the body weight daily either orally, subcutaneously, intramuscularly or intravenously.

25. The method of claim 24 wherein the hypercalchemia is vitamin D dependent rickets, hypoparathyroidism, post-operative renal osteodystorophy, liver cirrhosis, or steatorrhoea.

26. A method for treating osteoporosis, which comprises administering at least one of the 1α,24(S)- and 1α,24(R)-dihydroxycholecalciferols of formula (5-a)

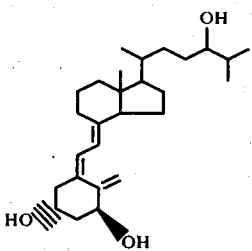
(5-a)

to a patient in a dosage of 0.01 to 10 μg per kilogram of the body weight per 24 hours either orally, subcutaneously, intramuscularly or intravenously.

27. A method for treating osteomalacia, which comprises administering at least one of 1α,24(S)- and 1α,24(R)-dihydroxycholecalciferols of formula (5-a)

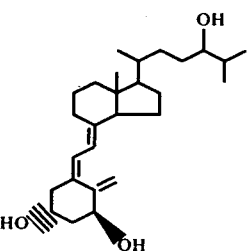
(5-a)

to a patient in a dosage of 0.01 to 10 μg per kilogram of the body weight per 24 hours either orally, subcutaneously, intramuscularly or intravenously.

28. A method for treating malabsorption syndrome, which comprises administering at least one of 1α,24(S)- and 1α,24(R)-dihydroxycholecalciferols of formula (5-a)

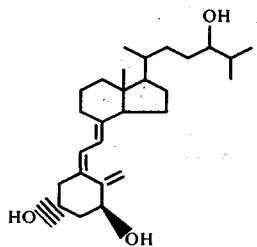
(5-a)

to a patient in a dosage of 0.01 to 10 μg per kilogram of the body weight per 24 hours either orally, subcutaneously, intramuscularly or intravenously.

29. A method for preventing hypocalcemia of domestic animals, which comprises administering at least one of 1α,24(S)- and 1α,24(R)-dihydroxycholecalciferols of formula (5-a)

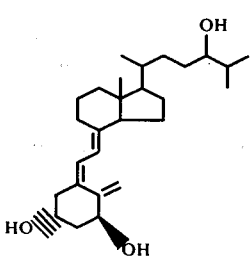
(5-a)

to a domestic animal.

30. A method for preventing the laying of soft-shelled eggs by poultry, which comprises administering at least one of 1α,24(S)- and 1α,24(R)-dihydroxycholecalciferols of formula (5-a)

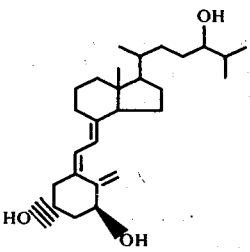
(5-a)

to poultry.

31. A feed for domestic animals and poultry comprising 0.2 to 20 g, per kilogram of the feed, of at least one of 1α,24(S)- and 1α,24(R)-dihydroxycholecalciferols of formula (5-a)

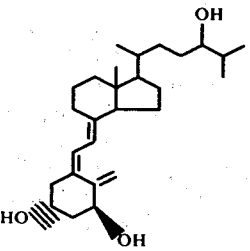
(5-a)

32. The method of claim 21 wherein the effective amount is from 0.04 to 0.4 mg. per kilogram of body weight, per day.

33. The method of claim 24 wherein the effective amount is from 0.04 to 0.4 mg. per kilogram of body weight per day.

34. The method of claim 26 wherein the effective amount is from 0.04 to 0.4 mg. per kilogram of body weight, per day.

35. The method of claim 27 wherein the effective amount is from 0.04 to 0.4 mg. per kilogram of body weight, per day.

36. The method of claim 28 wherein the effective amount is from 0.04 to 0.4 mg. per kilogram of body weight, per day.

* * * * *

UNITED STATES PATENT AND TRADEMARK OFFICE
CERTIFICATE OF CORRECTION

PATENT NO. : 4,022,891
DATED : May 10, 1977
INVENTOR(S) : TAKESHITA, ET AL.

It is certified that error appears in the above-identified patent and that said Letters Patent are hereby corrected as shown below:

Claim 6, column 42, line 6, delete "derivative" and insert
 -- derivatives --
Claim 8, line 2, delete "hydroxy" and insert -- hydroxyl --
Claim 14, column 44, line 40, delete "halogen" and insert
 -- halogen- --
Claim 23, line 1, delete "treting" and insert -- treating --
Claim 21, line 5, delete "(5a)" and insert -- (5-a) --

Signed and Sealed this twenty-sixth Day of July 1977

[SEAL]

Attest:

RUTH C. MASON
Attesting Officer

C. MARSHALL DANN
Commissioner of Patents and Trademarks